(12) United States Patent
Ramaiyan et al.

(10) Patent No.: US 12,036,535 B2
(45) Date of Patent: Jul. 16, 2024

(54) PEROVSKITE MATERIAL FOR METHANE TO ETHYLENE CONVERSION

(71) Applicant: UNM Rainforest Innovations, Albuquerque, NM (US)

(72) Inventors: Kannan Ramaiyan, Albuquerque, NM (US); Angelica Benavidez, Albuquerque, NM (US); Fernando Garzon, Albuquerque, NM (US); Luke Denoyer, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 0 days.

(21) Appl. No.: 18/320,931

(22) Filed: May 19, 2023

(65) Prior Publication Data

US 2023/0372911 A1 Nov. 23, 2023

Related U.S. Application Data

(60) Provisional application No. 63/343,887, filed on May 19, 2022.

(51) Int. Cl.
*B01J 23/847* (2006.01)
*B01J 23/00* (2006.01)
*B01J 23/20* (2006.01)
*C01G 33/00* (2006.01)
*C07C 2/84* (2006.01)

(52) U.S. Cl.
CPC ......... *B01J 23/8474* (2013.01); *B01J 23/002* (2013.01); *B01J 23/20* (2013.01); *C01G 33/006* (2013.01); *C07C 2/84* (2013.01); *C01P 2002/34* (2013.01); *C01P 2002/52* (2013.01); *C01P 2002/72* (2013.01); *C01P 2002/85* (2013.01); *C01P 2002/88* (2013.01); *C01P 2004/03* (2013.01); *C07C 2529/076* (2013.01)

(58) Field of Classification Search
None
See application file for complete search history.

(56) References Cited

U.S. PATENT DOCUMENTS

| | | | |
|---|---|---|---|
| 9,446,387 B2* | 9/2016 | Cizeron | B01J 35/19 |
| 2012/0041246 A1* | 2/2012 | Scher | C01G 31/02 |
| | | | 502/305 |
| 2013/0158322 A1* | 6/2013 | Nyce | C07C 11/04 |
| | | | 585/662 |
| 2014/0107385 A1* | 4/2014 | Schammel | B01J 8/001 |
| | | | 585/501 |
| 2017/0267605 A1* | 9/2017 | Tanur | B01J 37/04 |

OTHER PUBLICATIONS

Suresh Mulmi and Venkataraman Thangadurai, "Preparation, Structure and CO2 Sensor Studies of $BaCa_{0.33}Nb_{0.67-x}Fe_xO_{3-\delta}$," Journal of The Electrochemical Society, 160 (8) B95-B101 (2013).

R. Kannan, S. Mulmi and V. Thangadurai "Synthesis and characterization of perovskite-type $BaMg_{0.33}Nb_{0.66-x}Fe_xO_{3-\delta}$ for high temperature $CO_2$ sensors" Journal of Materials Chemistry A, 2013, 1, 6874-6879.

* cited by examiner

*Primary Examiner* — Ali Z Fadhel
(74) *Attorney, Agent, or Firm* — Keith Vogt, Ltd.; Keith A. Vogt

(57) ABSTRACT

A catalyst comprising a barium niobate-based cubic perovskite structure where, Mg and Ca has been used to dope the niobium sites along with Fe, Ni, Co, Y, and Pr.

21 Claims, 15 Drawing Sheets

PEROVSKITE MATERIAL FOR METHANE TO ETHYLENE CONVERSION

RELATED APPLICATIONS

This application claims priority to U.S. Provisional Application No. 63/343,887, filed on May 19, 2022, which is incorporated herein in its entirety.

STATEMENT REGARDING FEDERALLY SPONSORED RESEARCH & DEVELOPMENT

Not applicable.

INCORPORATION BY REFERENCE OF MATERIAL SUBMITTED ON A COMPACT DISC

Not applicable.

BACKGROUND OF THE INVENTION

Methane is the major component of many gas sources such as natural gas and shale gas and more than 500 million tons of methane is produced every year. Oxidative and non-oxidative coupling of methane (OCM and NOCM) have been actively researched to produce ethylene and higher olefins from methane for few decades although catalysts with commercially viable conversion rates have not yet been developed. Electrochemical OCM (E-OCM) is gaining attention due to its ability to regulate the oxide ion flux that will help reduce the over-oxidation of methane while also helping to activate methane. Fe-based catalysts have been shown to activate methane in both OCM and NOCM although suffer from coking-related durability challenges.

Methane conversion into value-added products such as olefins and aromatics is gaining increased attention in the wake of new natural gas reserve discoveries. E-OCM provides better product selectivity as the product distribution can be controlled by applied potential as well as the oxide ion flux.

Efficient on-site conversion of methane to value-added chemicals such as ethylene and higher hydrocarbons is also an active area of research as many recent discoveries of natural gas reserves made methane a cheap source of energy with an estimated reserve volume of 215 trillion cubic meters (TCM) worldwide. Due to these new discoveries, methane prices have dropped from $7-9 USD per million BTU in 2008 to roughly $2 USD per million BTU in 2020. Readily available amounts of natural gas have risen over 30% in the past 20 years although transporting it to retail locations remains challenging.[4] Difficulties in transportation of natural gas has resulted in onsite venting and flaring of methane, which results in the release of greenhouse gases $CH_4$ and $CO_2$ to the environment apart from methane being wasted. Hence, direct conversion of methane to ethylene is highly desired due to ethylene's use as a building block for valuable commodity chemicals, in a wide variety of chemical industries.

Current technology for producing ethylene primarily centers around naphtha steam-cracking, employing high temperature steam-cracking process as a primary method (>750° C.), which incurs large energy losses and produces significant amounts of $CO_2$. Direct catalytic conversion of methane to ethylene allows for skipping of multiple steps that must be completed during steam cracking. For example, direct non-oxidative coupling of methane (NOCM) features methane coupling without requiring an oxygen source into ethylene and aromatic compounds. However, NOCM requires high operating temperatures and suffers from ill-defined catalyst mechanisms and significant coke formation.

Low temperature oxidative coupling of methane (OCM) considers methane coupling at temperatures (~750° C.) in low $O_2$ (or other oxidizing agents) gas environments on a catalyst surface.

Under OCM conditions, methane coupling to a partial oxidation product such as ethylene is thermodynamically feasible, although further oxidation products like CO and $CO_2$ are even more favorable. In addition, reaction between the desired product, $C_2H_4$ and oxygen to produce $CO_2$ (−1294 kJ/mol at 800° C.) is far more energetically facile in comparison to methane oxidation to produce $CO_2$ (−800 kJ/mol at 800° C.) predicted from HSC calculations (Collected using HSC Chemistry version 10.0.5.16 software from Outotec®). Hence difficulty in achieving ethylene selectivity has remained an issue for OCM.

A novel method attempting to circumvent the over-oxidation of methane to $CO_2$ is the electrochemical oxidative coupling of methane (E-OCM). The fine-tuning of potential within an electrochemical cell allows for the regulation of oxide ion flux from cathode to anode across the electrolyte material. Further, the extent of oxidation can also be manipulated by the applied bias. Thus E-OCM can theoretically help achieve the partial oxidation of methane to ethylene using oxide-ion conducting electrolytes while restricting the over-oxidation to undesirable products like CO and $CO_2$. Another recent consideration is using an Fe doped strontium molybdate (SFMO) perovskite catalyst that selective partial oxidation to ethylene is preferred at a specific electrochemical window during E-OCM.

Nevertheless, SFMO materials suffered from poor chemical stability under the operating conditions of E-OCM as strontium formed strontium carbonate upon exposure to methane along with significant coke formation. This is a major challenge for many newly developed electrolyte and electrocatalyst systems under high temperature operations and redox stability is essential for durable operation of these devices.

BRIEF SUMMARY OF THE INVENTION

In one embodiment, the present invention provides a catalyst, device, system and method concerning a barium niobate-based perovskite system for effective E-OCM, where, Mg and Ca has been used to dope the niobium sites along with Fe, Ni, Co, Y, and Pr.

In another embodiment, the present invention provides a catalyst, device, system and method concerning a barium niobate-based perovskite system wherein the perovskite is Fe and Mg co-doped $BaMg_{0.33}Nb_{0.67-x}Fe_xO_{3-\delta}$ (BMNF) perovskite for effective E-OCM, where, Mg and Ca has been used to dope the niobium sites along with Fe.

In another embodiment, the present invention provides a catalyst, device, system and method wherein the chemical formula of these compounds is $BaCa_{0.33}Nb_{0.67-x}M_xO_{3-\delta}$ and $BaMg_{0.33}Nb_{0.67-x}M_xO_{3-\delta}$ where M is one or more of Fe, Co, Ni, Y, or Pr and the M content is varied from x=0 to x=33 and Ca is varied between 0.20 to 0.40.

In another embodiment, the present invention provides a catalyst, device, system and method wherein the chemical formula of these compounds is $BaCa_{0.33}Nb_{0.67-x}M_xO_{3-\delta}$ and $BaMg_{0.33}Nb_{0.67-x}M_xO_{3-\delta}$ where M is one or more of Fe, Co, Ni, Y, or Pr and the M content is varied from x=0 to x=60 and Ca is varied between 0.20 to 0.40.

In another embodiment, the present invention provides a catalyst, device, system and method of claim 1 wherein the incorporation of Fe or other transition metal ions in the crystal lattice results in mixed ionic electronic conductivity enabling electron and ionic transport to achieve effective E-OCM activity.

In another embodiment, the present invention provides a new catalyst based on Mg and Fe co-doped barium niobate perovskites. The perovskites of the present invention show excellent chemical stability in $CH_4$-rich environments up to 925° C. while showing methane activation properties from 600° C. E-OCM measurements indicated an ethylene production rate of 277 µmol $cm^{-2}$ $h^{-1}$ with a faradaic efficiency of 20% at 1 V and durable operation for six continuous days. XPS measurements indicate significant Nb valency reorganization providing chemical stability. The exceptional chemical stability of this perovskite material under methane exposure at high temperatures has significant importance as this material could be used as a catalyst and/or support in a wide variety of applications relevant for efficiency energy conversion and storage.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

DETAILED DESCRIPTION OF THE INVENTION

Figure 1A:
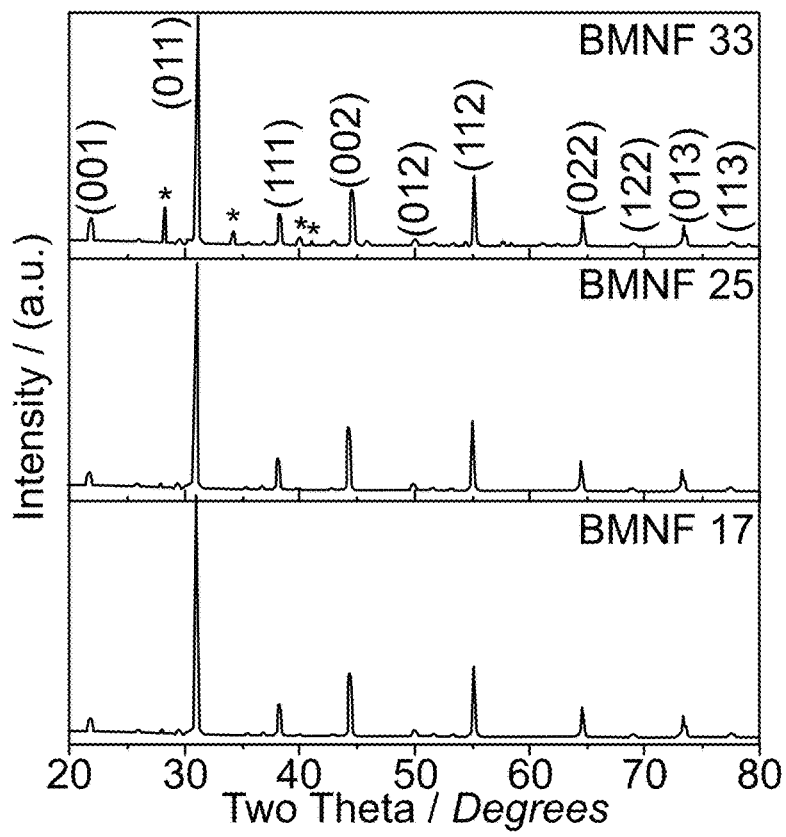
FIG. 1A shows PXRD patterns obtained for the as-prepared BMNF materials with various Fe doping.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure, or system. Further, the terms and phrases used herein are not intended to be limiting but rather to provide an understandable description of the invention.

In a preferred embodiment, the present invention concerns a barium niobate based perovskite system for effective E-OCM, where, Mg and Ca has been used to dope the niobium sites along with Fe. The chemical formula of these compounds is $BaCa_{0.33}Nb_{0.67-x}Fe_xO_{3-\delta}$ and $BaMg_{0.33}Nb_{0.67-x}Fe_xO_{3-\delta}$ where the Fe content is varied from x=0 to x=33. In another embodiment, the chemical formula of these compounds is $BaCa_{0.33}Nb_{0.67-x}Fe_xO_{3-\delta}$ and $BaMg_{0.33}Nb_{0.67-x}Fe_xO_{3-\delta}$ where the Fe content is varied from x=0 to x=60 and where Ca is varied between 0.20 and 0.40.

This class of materials due to the incorporation of Fe in the crystal lattice show mixed ionic electronic conductivity that is essential for electron and ionic transport to achieve effective E-OCM activity. Their physical and chemical properties evaluated using TGA, XRD, XPS and FT-IR measurements demonstrate very good chemical stability under E-OCM conditions. TGA under methane environment further reveal adsorption of methane in a perovskite material at about 600° C.

The catalysts were further examined for E-OCM along with structural and chemical stability characterizations. Ethylene production was observed to increase with increasing Fe content in the perovskite structure.

Fe and Mg co-doped $BaMg_{0.33}Nb_{0.67-x}Fe_xO_{3-\delta}$ (BMNF) perovskite material has been demonstrated to resist the carbonate formation under $CO_2$ environments at elevated temperatures. Further, Fe is incorporated in the crystal lattice and hence should resist coke formation unlike Fe—O based catalyst systems that form carbide and coke in carburizing environments.[29] This is highly relevant for E-OCM which involves exposure to $CH_4$, and $CO_2$ at elevated temperatures, Thus, this material was tested for chemical stability and E-OCM conversion with three different iron doping levels (x=0.33, 0.25, and 0.17 (BMNF33, BMNF25, and BMNF17 respectively)).

Specifically, these powders were exposed to pure methane at temperatures up to 925° C. and studied their PXRD patterns before and after exposure. Electrochemical measurements were carried out in a home-made button cell set up. For electrochemical measurements, BMNF with varying Fe content in combination with Gd doped Ceria (GDC) in a 65:35 ratio was used as the anode while $Sr_2Fe_{1.5}Mo_{0.5}O_{6-\delta}$ (SFMO) mixed with GDC in 65:35 ratio was used as the cathode. LSGM pellets with a 0.9 mm thickness and 20 mm diameter were utilized as the electrolyte. E-OCM measurements were carried out at 850° C. and 925° C. at methane flow rates of 100 SCCM to the anode and $O_2$ flow rates of 100 SCCM to the cathode. Silver mesh and gold wires were used as current collectors. Electrochemical measurements were also carried out in 4% $H_2$ balanced in $N_2$ for comparison purposes.

One of the major challenges for many metal oxide electrodes studied for E-OCM is their chemical stability in carbon-rich environments under high operating temperatures relevant for E-OCM. Hence, investigating the crystallinity of the prepared BMNF materials before and after exposure to methane at elevated temperatures is key in assessing the likelihood of the perovskite to maintain its structure in highly reducing methane environments. The current operating temperatures for the electrochemical oxidative coupling cells may reach as high as 925° C. for testing purposes, with durability tests being done at a maximum of 925° C. for multiple days. However, reducing the operating temperature to as low as 600° C. is increasingly sought after in recent times.

All three prepared BMNF compositions (x=0.17, 0.25, and 0.33) were exposed to methane in a TGA set up and analyzed them through PXRD before and after exposure to $CH_4$. TGA in air environment is also recorded for comparison purposes. PXRD patterns obtained for as-prepared BMNF powders are shown in FIG. 1a, which displays the formation of cubic perovskite structure with a space group=Pm-3m (No. 221).

However, with higher Fe doping as in BMNF33, impurity peaks at two theta values of 27° and 340 degrees were observed.

Figure 1B:
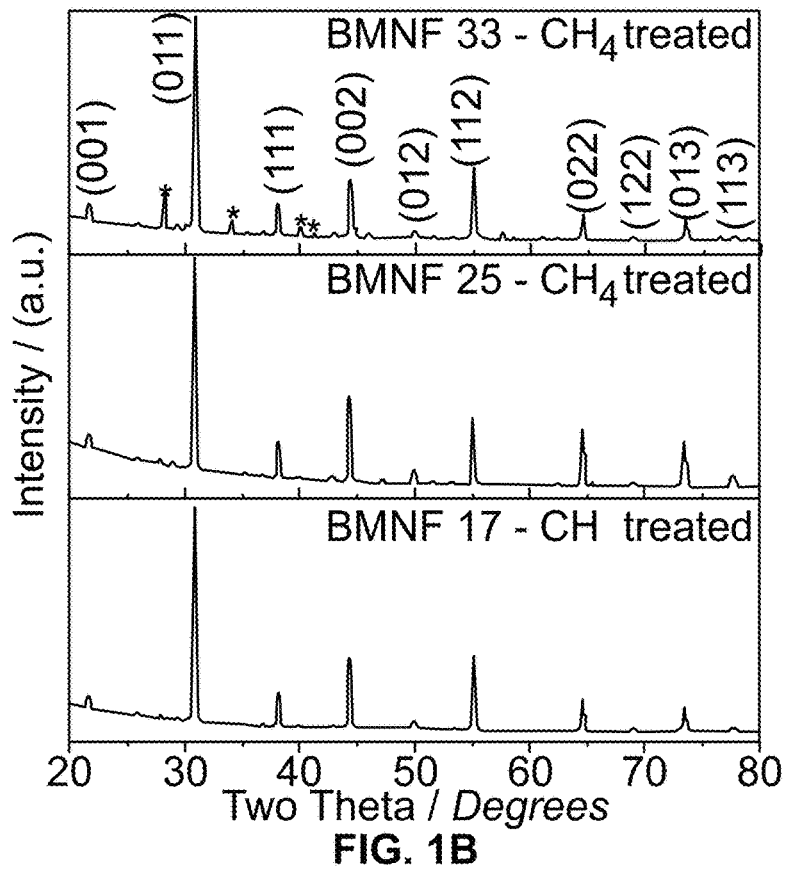
FIG. 1B shows PXRD patterns of BMNF materials after exposure to pure methane at 900° C.
Figure 1C:
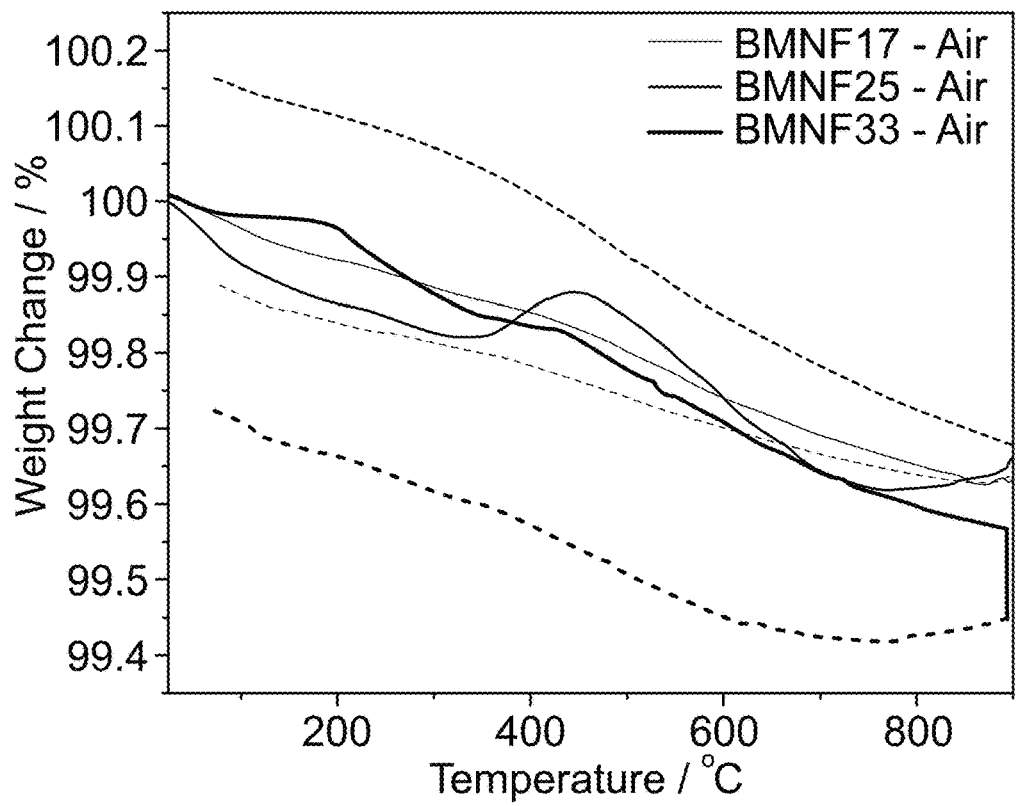
FIG. 1C shows TGA plots obtained for the as prepared BMNF powders in an air atmosphere.
Figure 1D:
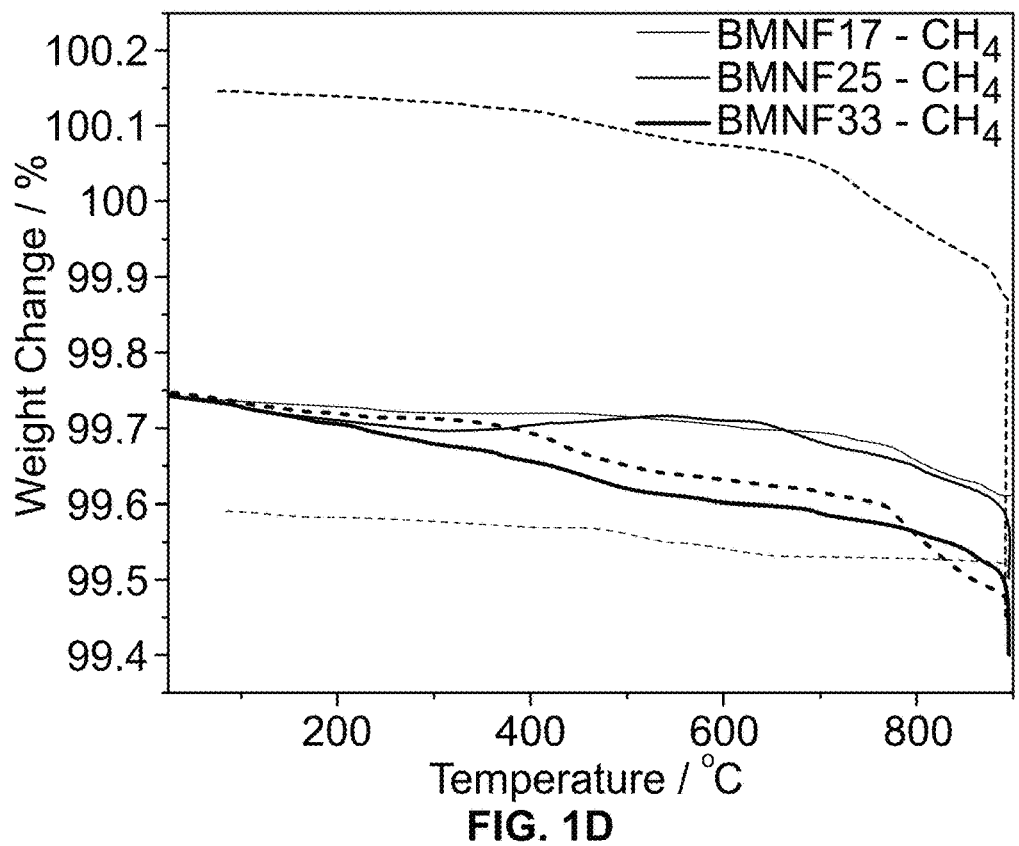
FIG. 1D shows TGA plots obtained for BMNF powders in pure methane atmosphere. The TGA curves in solid indicate the heating direction and curves in dots indicate the cooling response.

With the incorporation of smaller $Fe^{3+}$ ions over $Nb^{5+}$, the peak positions shifted towards higher two theta values as expected from their Shannon ionic radii. TGA measurements carried out in air in the temperature range of 25° C. to 900° C. did not show any significant weight change with a maximum weight loss of 0.4% observed for BMNF33 after holding at 900° C. for one hour (FIG. 1c). This could be due to some lattice oxygen lost in equilibrating with its environment. TGA measurements under similar heating conditions in pure $CH_4$ environment showed similar weight changes with a maximum weight gain of 1.75% observed for BMNF25 while BMNF33 showed a maximum weight loss of 1% at 900° C. (FIG. 1d). The marginally higher weight loss under $CH_4$ environment (1% in $CH_4$ vs 0.4% in air) could be due to the lattice oxygen on the exposed surface reacting with methane and as a result leaving the crystal structure. The lack of weight gain indicates the possible lack of coke formation during the TGA measurements.

SFMO powders under similar operating conditions showed a weight gain of about 40 to 60% that was associated with significant coke formation and crystal structure collapse. To investigate any possible change to crystal structure, the $CH_4$ exposed powders in PXRD were analyzed. As shown in FIG. 1b, the cubic perovskite structure is retained in all three samples and do not show any new peak formation or change in the peak positions associated with the cubic perovskite structure. Interestingly, the impurity peaks observed in the as-prepared BMNF33 also retained their position and relative intensity after exposure to methane in the TGA set up. The ratio between peaks in both as-prepared powders and $CH_4$ exposed samples remained the same indicating the complete crystallinity retention. Thus, PXRD measurements in combination with TGA provide the first evidence of significant chemical stability for the BMNF material in E-OCM operating conditions. This is in complete contrast to the SFMO powders that formed $SrCO_3$, $SrMO_x$, and $MoO_xC_y$ upon exposure to methane under similar operating conditions.

Similar to SFMO, the expected reactions for the constituents of BMNF perovskites such as Ba and Mg upon exposure to methane was the formation of carbonates such as $BaCO_3$, and to some extent $MgCO_3$ along with agglomeration of carbon (coking) on the surface that would result in significant weight gain. However, the cubic BMNF perovskite material showed no significant weight change along with complete retention of its crystal structure as observed from FIG. 1a to 1d.

The stability of the BMNF structure in methane environment is important due to the constant methane supply to the electrode, and evolution of carbon products such as $C_2H_4$, CO, and $CO_2$ during OCM and E-OCM processes. High temperature operations render carbonate formations on Mg oxide surface as unfavorable, but unless E-OCM is being used to control the flux of oxide ions within the electrochemical cell, OCM may nevertheless lead to the formation of $BaCO_3$. The Gibbs free energy of reaction for $CO_2$ is $\Delta G_R \approx -800$ kJ mol$^{-1}$ throughout the temperature range being tested (800-900° C.) and would be the dominant product if the reaction is not controlled specifically to produce partial oxidation product such as ethylene by oxide ion flux and applied potentials. To understand this, temperature programmed reaction measurements were carried out where first the BMNF25 powder was exposed to a gas mixture containing 95% $CH_4$ and 5% $O_2$. The exposed powder was analyzed for $BaCO_3$ and coke formation while the outlet stream was analyzed by mass spectroscopy.

Temperature Programmed Reaction of $CH_4$ and $O_2$ on BMNF

Temperature programmed reaction (TPR) measurements under gas mixtures of $CH_4$ and $O_2$ on a catalyst surface will help evaluate the onset temperature of catalytic activity of a new catalyst towards oxidative coupling of methane and provide information about the product distribution. The TPR measurements were taken by passing a mixture of 95% $CH_4$: 5% $O_2$ at a flow rate of 100 SCCM and a heating rate of 5° C./min to 925° C. followed by a hold at 925° C. for one hour.

Figure 2:
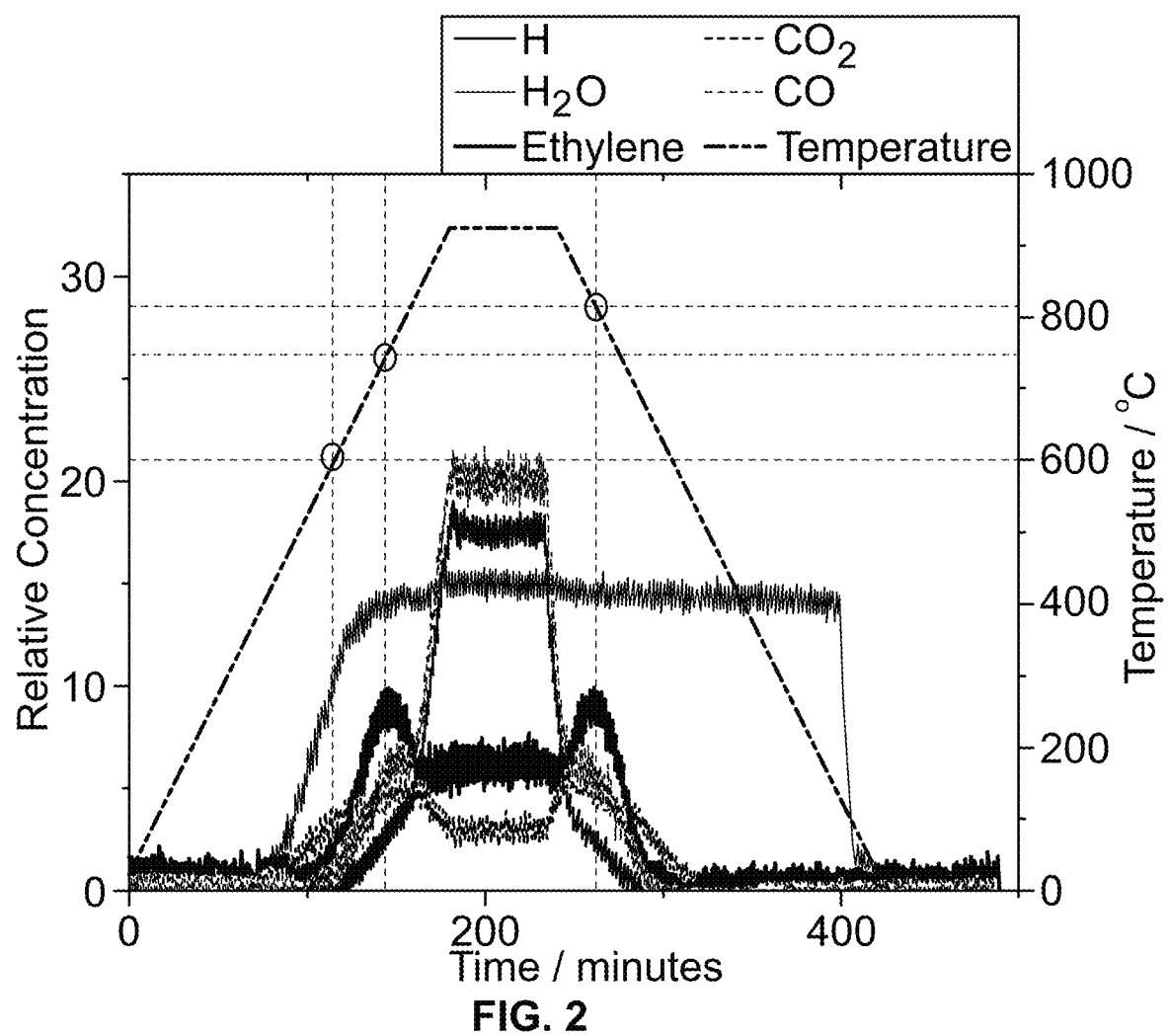
FIG. 2 shows mass spectroscopic plots obtained for the outlet stream during TPR measurements for the BMNF33 sample in the temperature range of 25-925° C. under 95% $CH_4$ and 5% $O_2$.

Reported TPR measurements on SFMO under three different $CH_4$ to $O_2$ ratios (100% $CH_4$, 95% $CH_4$: 5% 02, and 90% $CH_4$: 10% $O_2$) revealed maximum coke formation (100% weight gain) under the 95% $CH_4$: 5% $O_2$ mixture. SFMO perovskites showed coke formation to start at 800° C. along with other products such as CO, $CO_2$, $H_2$ and small quantities of ethylene. Mass spectra analysis on the outlet stream of TPR measurements obtained with BMNF33 is given in FIG. 2, where the onset of ethylene production starts at temperatures as low as 600° C. and reaches the maximum in the temperature range of 750-800° C. One of the most studied catalyst for OCM reaction, Mn—$Na_2WO_4$, is reported to show methane conversions at 800° C. at much higher $CH_4$ to $O_2$ ratio.[m] Hence, a much lower onset temperature of 600° C. for BMNF33 indicates an ability for reducing the OCM operating temperatures. Interestingly, the contribution from CO and $CO_2$ is comparatively smaller than that of ethylene in this temperature range. However, further increase in temperature results in increased CO production. This could be due to a multitude of factors. For example, at about 900° C., the dry reformation of methane ($CH_4+CO_2=2CO+H_2$) becomes thermodynamically preferred reaction that could explain the rise in CO and $H_2$ concentration while that of ethylene and $CO_2$ decrease. Also, ethylene is more reactive than methane in general and the decline in ethylene concentration could also be due to possible reaction between produced ethylene and oxygen leading to increased CO production. For comparison, a bare tube measurement with no catalyst in the temperature range of 25-900° C. was ran. No gas phase reactions take place till the temperature reached about 875° C. At 900° C. The product stream is dominated by $H_2O$, CO and $H_2$ with smaller contributions from ethylene and $CO_2$. HSC calculation involving 95% $CH_4$ and 5% $O_2$ in the investigated temperature range indicated the CO to be the major product at temperatures above 600° C. although this process could be kinetically limited. The above provided results indicate the catalytic activity of BMNF perovskites to activate methane towards ethylene production with higher selectivity in the temperature range of 600-800° C. The carbon atom balance during the TPR measurement is close to 100% reiterating the lack of coke formation with this catalyst. A maximum conversion of 12.5% and a selectivity of 50.3% was observed from BMNF33 catalyst at 800° C. The weight gain measurements carried out on the sample before and after TPR measurements did not reveal any weight gain further indicating the absence of coking.

Electrochemical Properties of BMNF Materials

Figure 3A:
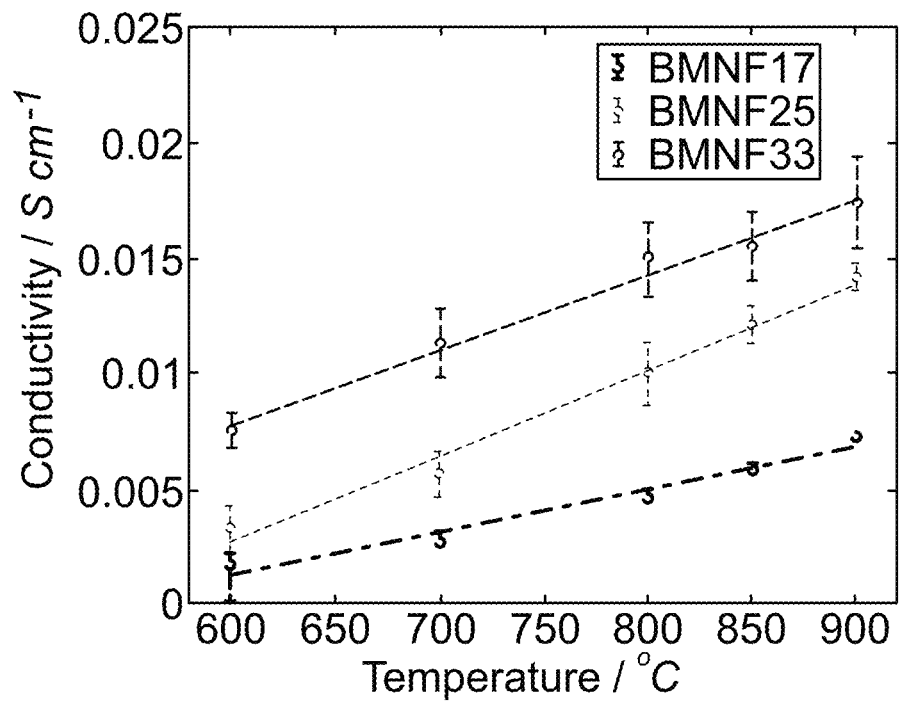
FIG. 3A shows conductivity data obtained for the three BMNF pellets in the temperature range of 600 to 900° C.
Figure 3B:
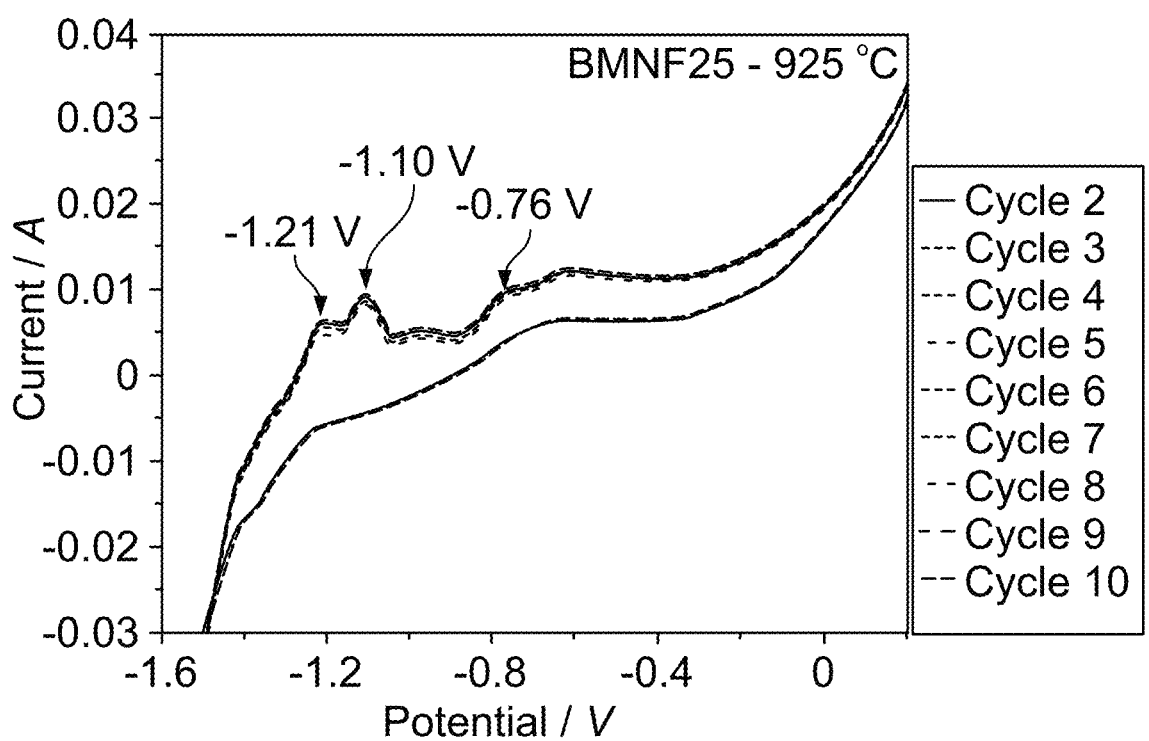
FIG. 3B shows cyclic voltammetry curves obtained for BMNF25 under $CH_4$ cathode environment.
Figure 3C:
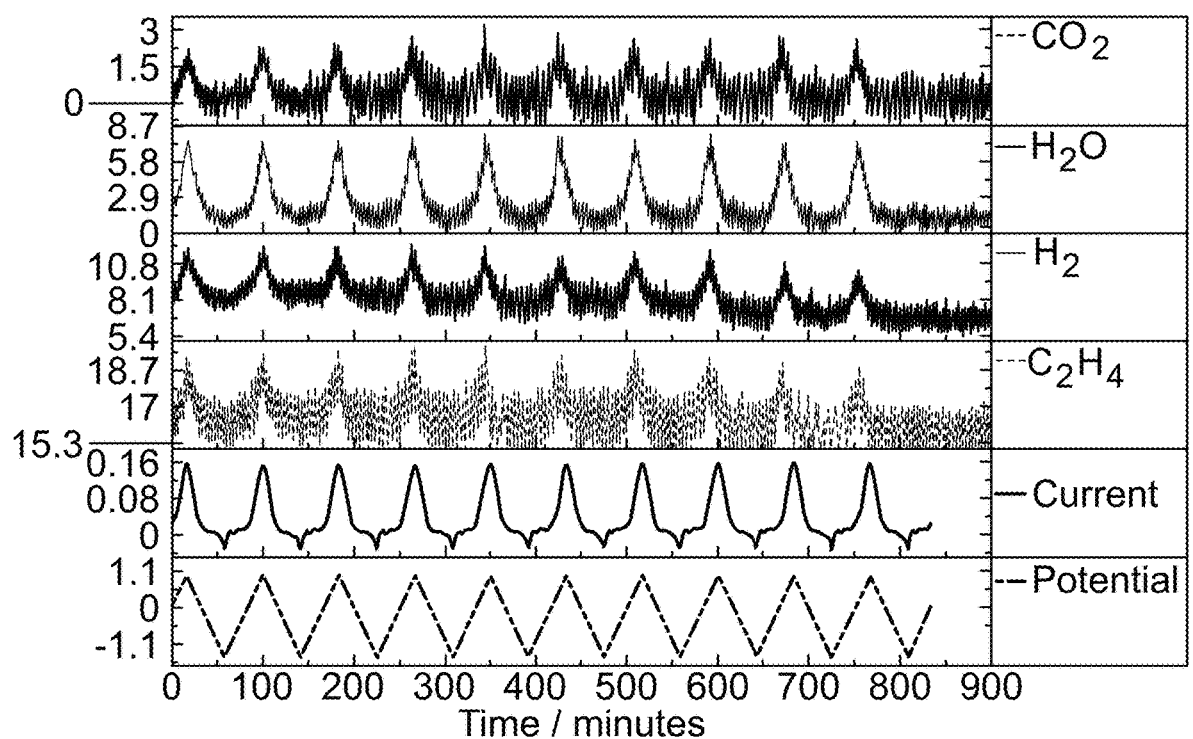
FIG. 3C shows current and potential curves along with observed product stream as a function of time for the CV curve.
Figure 4:
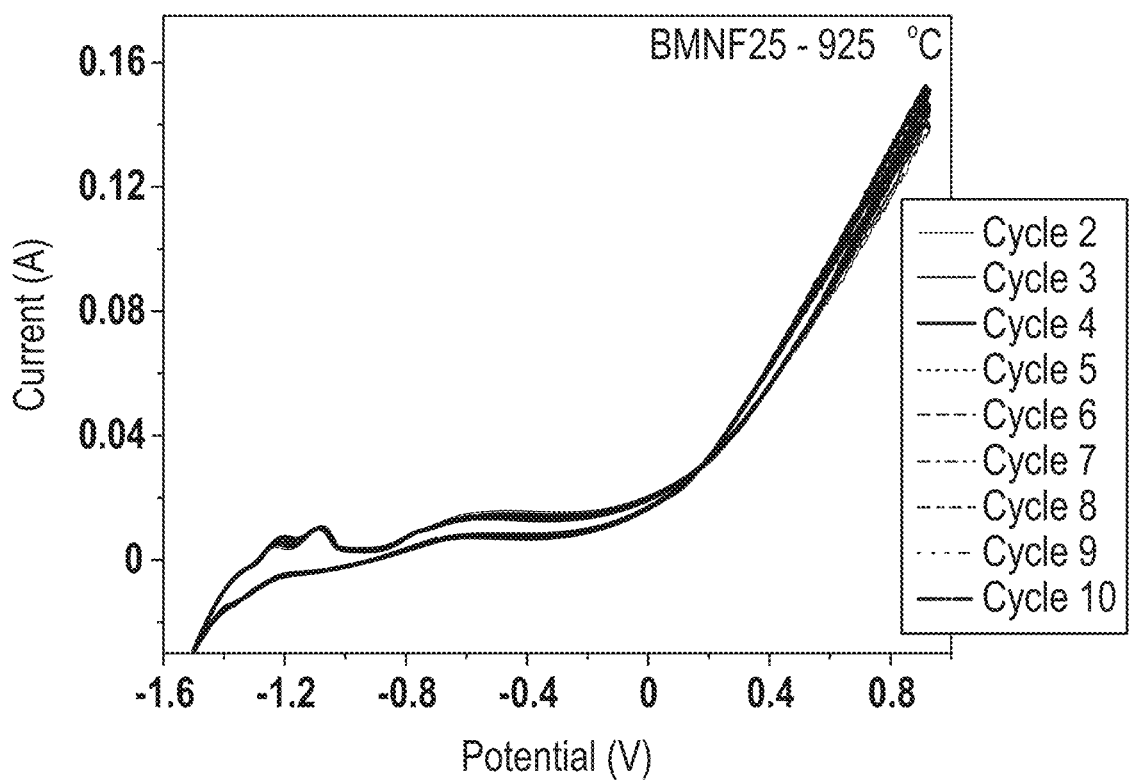
FIG. 4 is a cyclic voltammetry plot obtained for BMNF25 at 925° C. in a wide potential window of −1.5V to 1.0V at a scan rate of 1 mV/s in anode $CH_4$ environment. The air electrode was utilized as the reference electrode.
Figure 5:
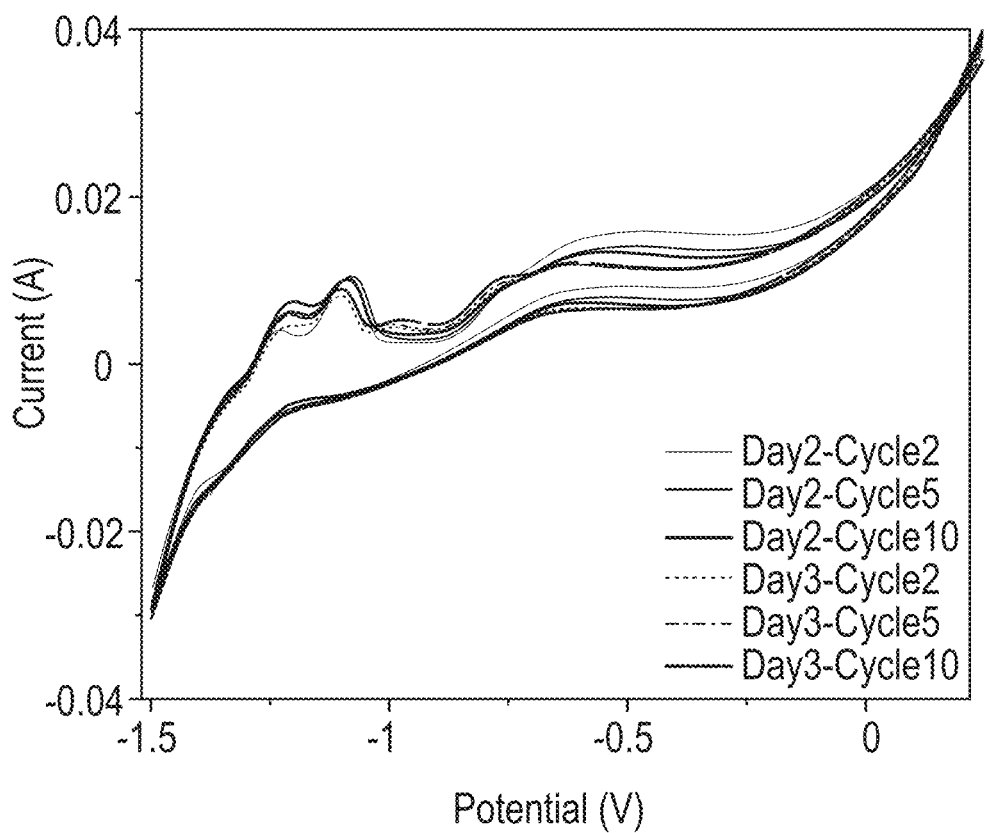
FIG. 5 shows CV curves obtained for BMNF25 at 925° C. in a wide potential window of −1.5V to 1.0V at a scan rate of 1 mV/s in anode $CH_4$ environment under continuous operation for three days.
Figure 6:
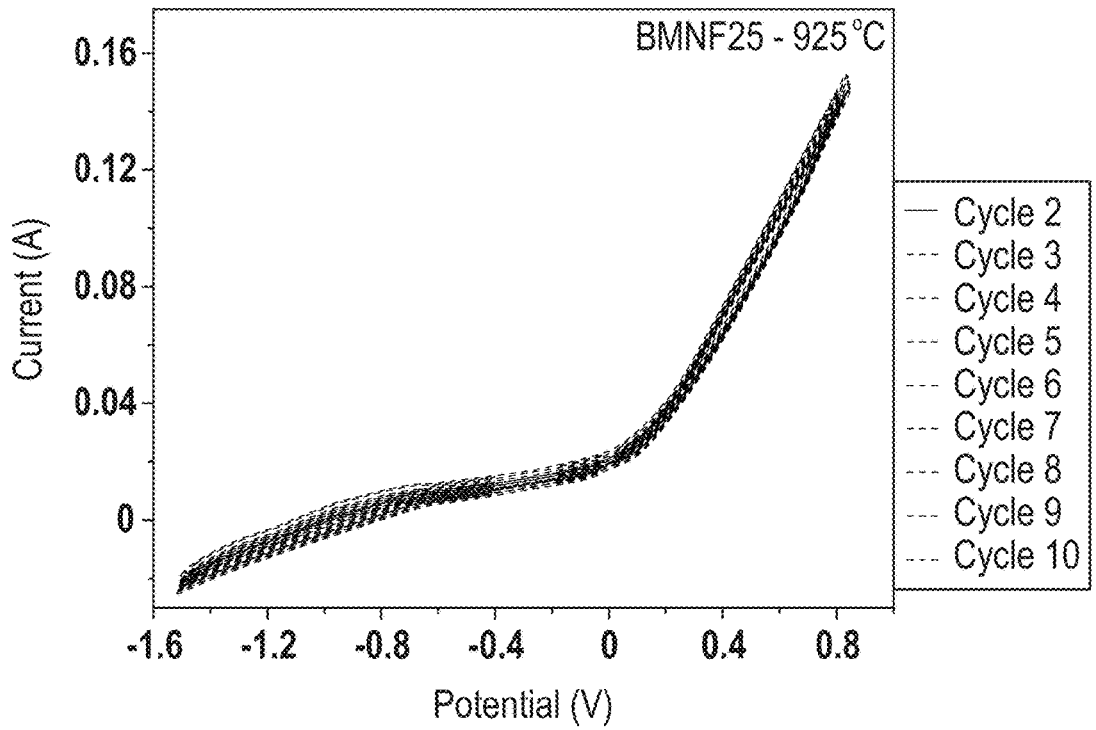
FIG. 6 shows CV curves obtained for BMNF25 at 925° C. in a wide potential window of −1.5V to 1.0V at a scan rate of 1 mV/s in anode 4% $H_2$ environment.
Figure 7:
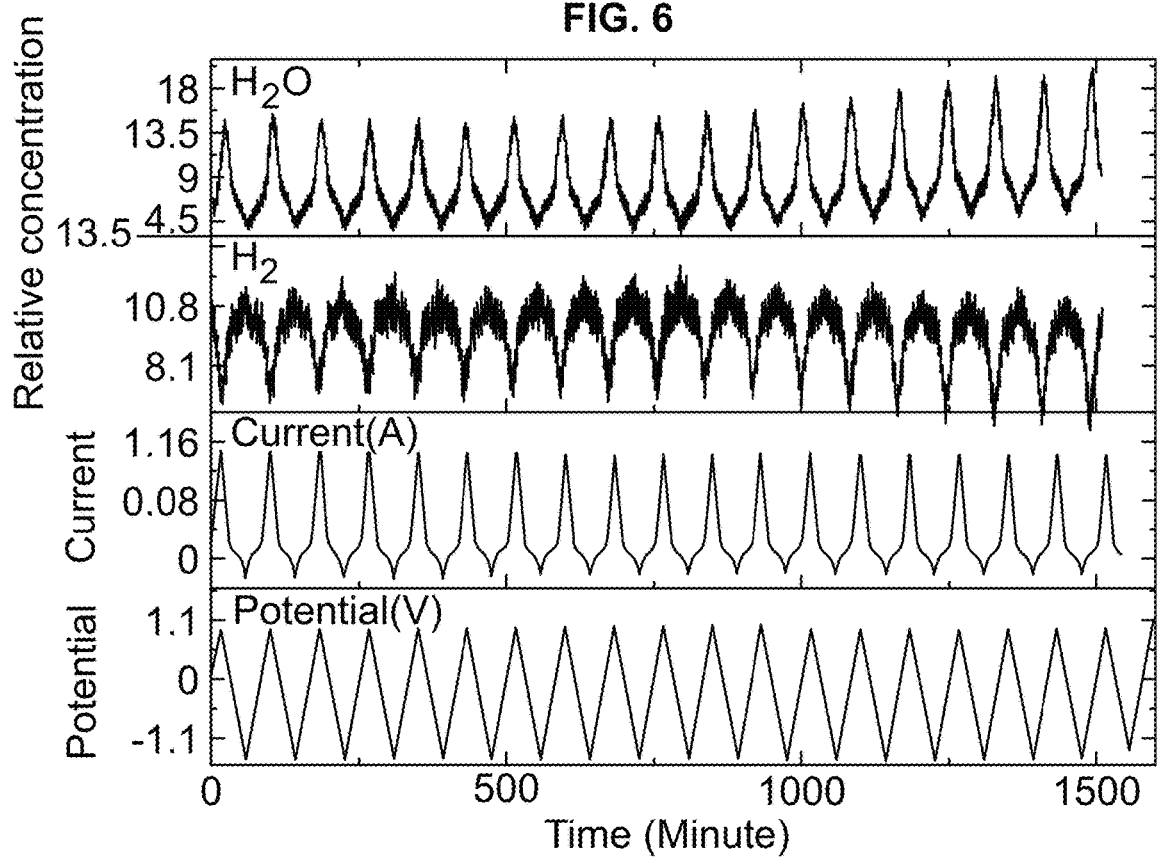
FIG. 7 shows current and potential curves along with observed product stream as a function of time for the CV curve presented in FIG. 6.
Figure 8A:
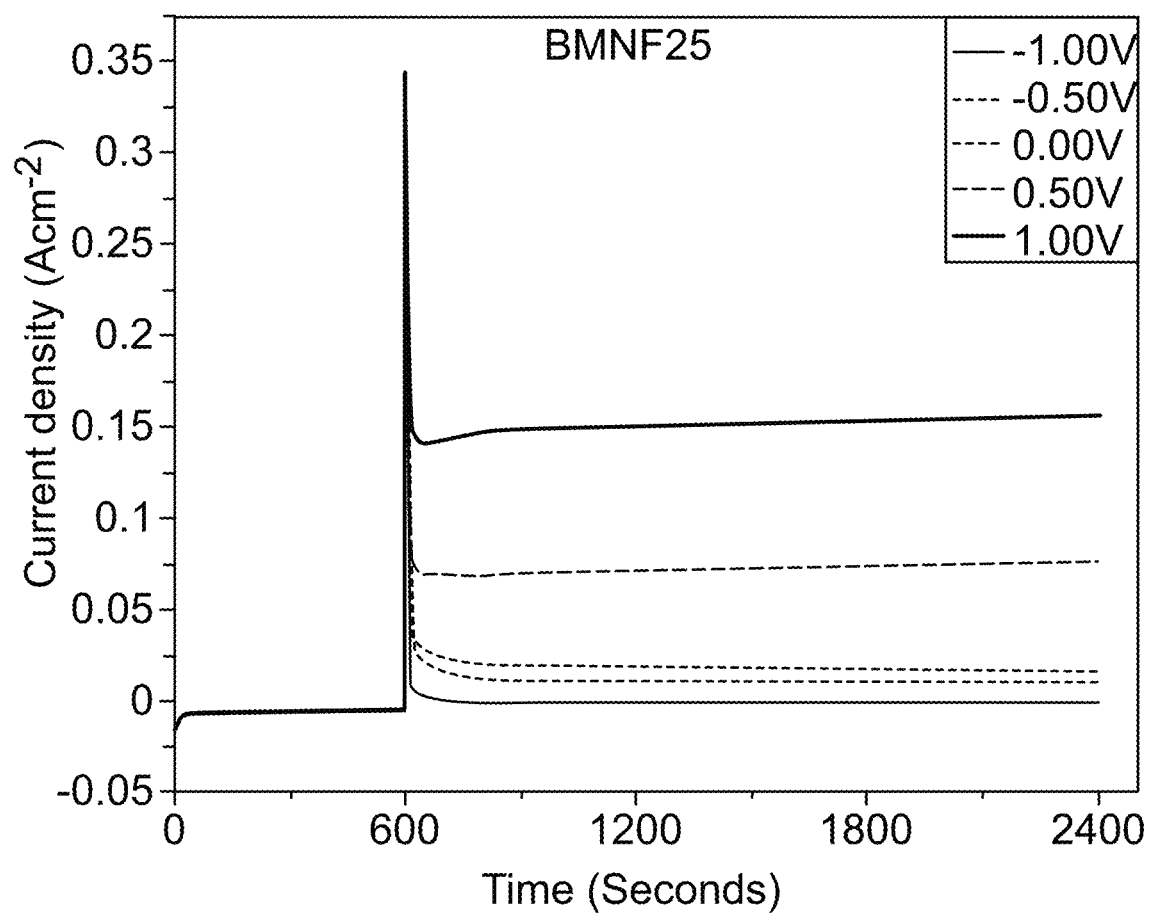
FIGS. 8A, 8B, 8C, 8D, and 8E provide chronoamperometric data obtained for BMNF25 cell, (a) I-V plots obtained via the CA measurements, mass spec data obtained for the outlet stream during CA measurement for (b) $H_2$, (c) $C_2H_4$, (d) $H_2O$, and (e) $CO_2$.
Figure 8B:
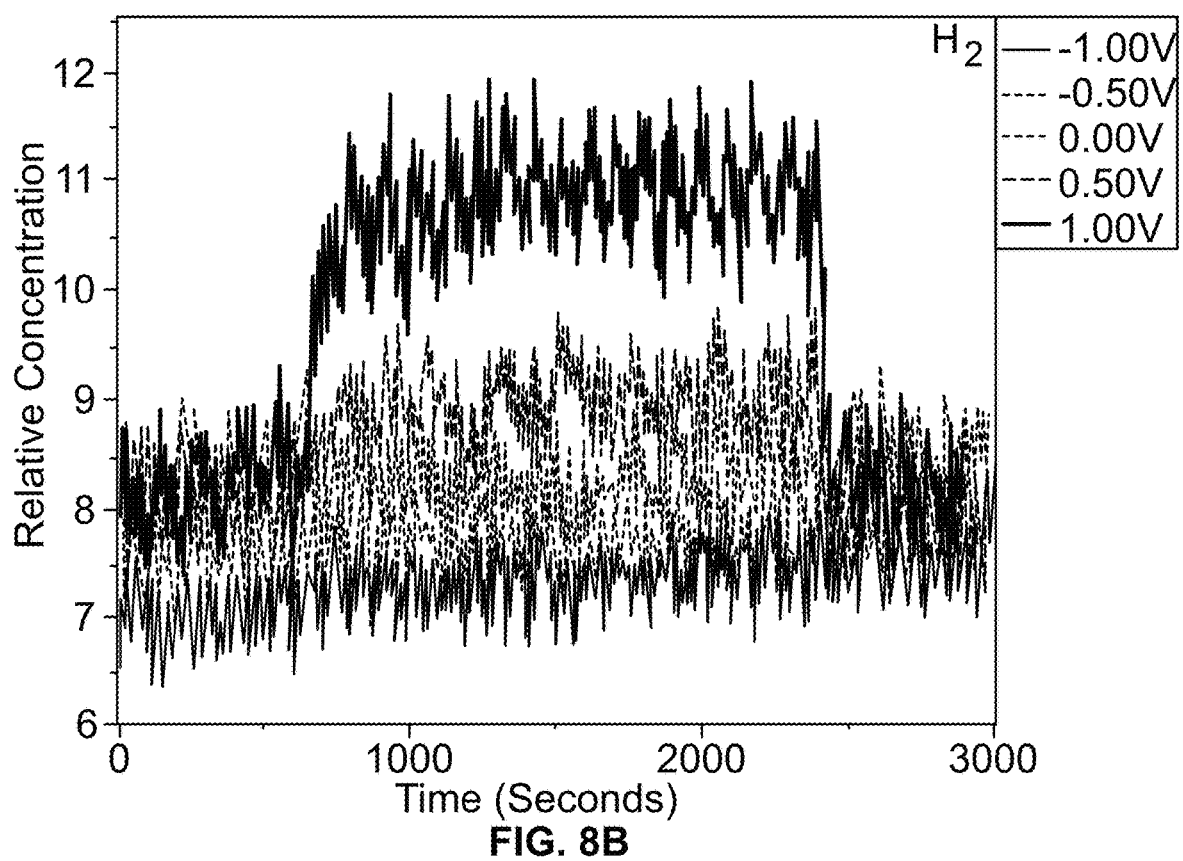
Figure 8C:
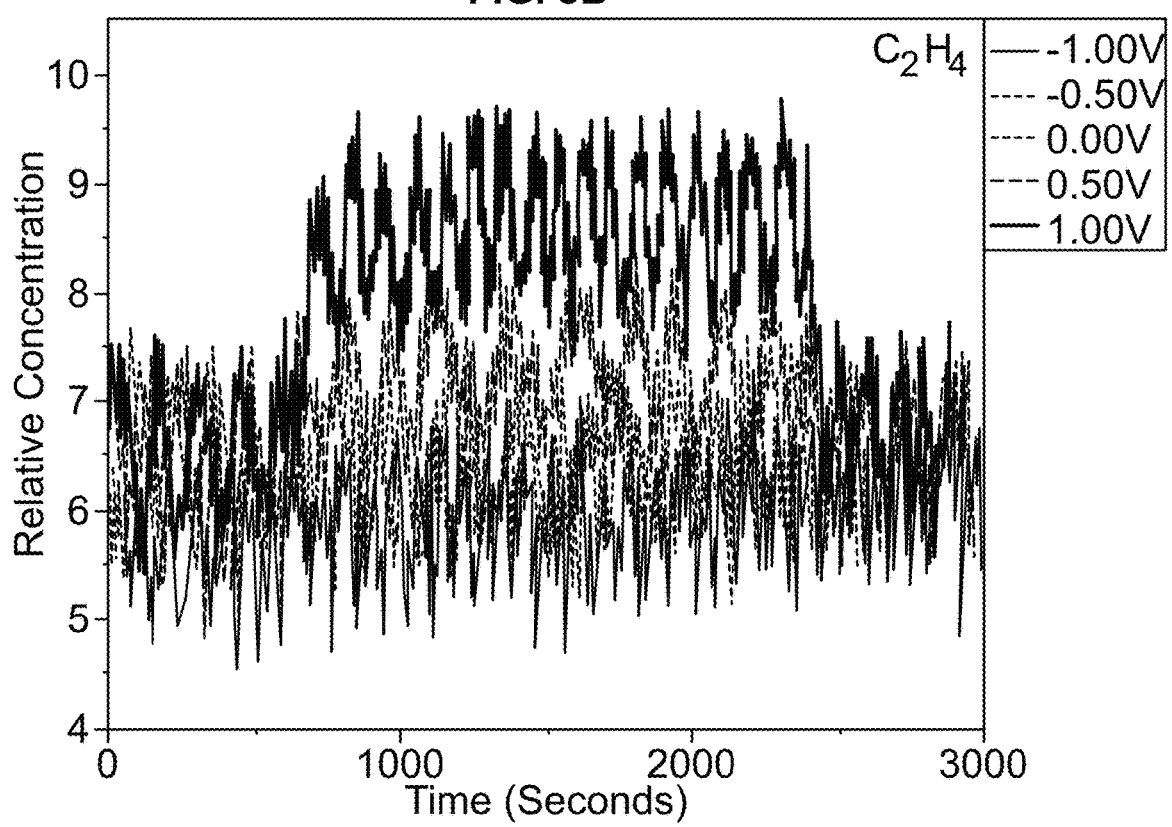
Figure 8D:
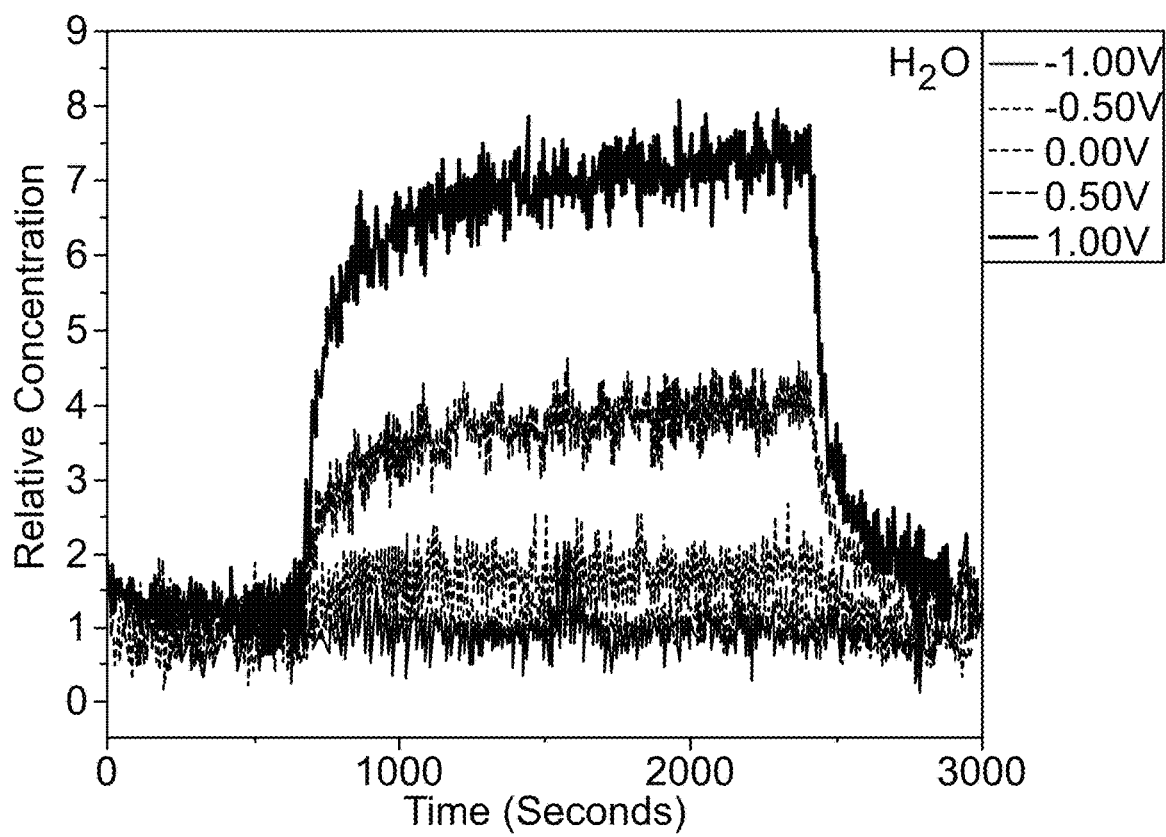
Figure 8E:
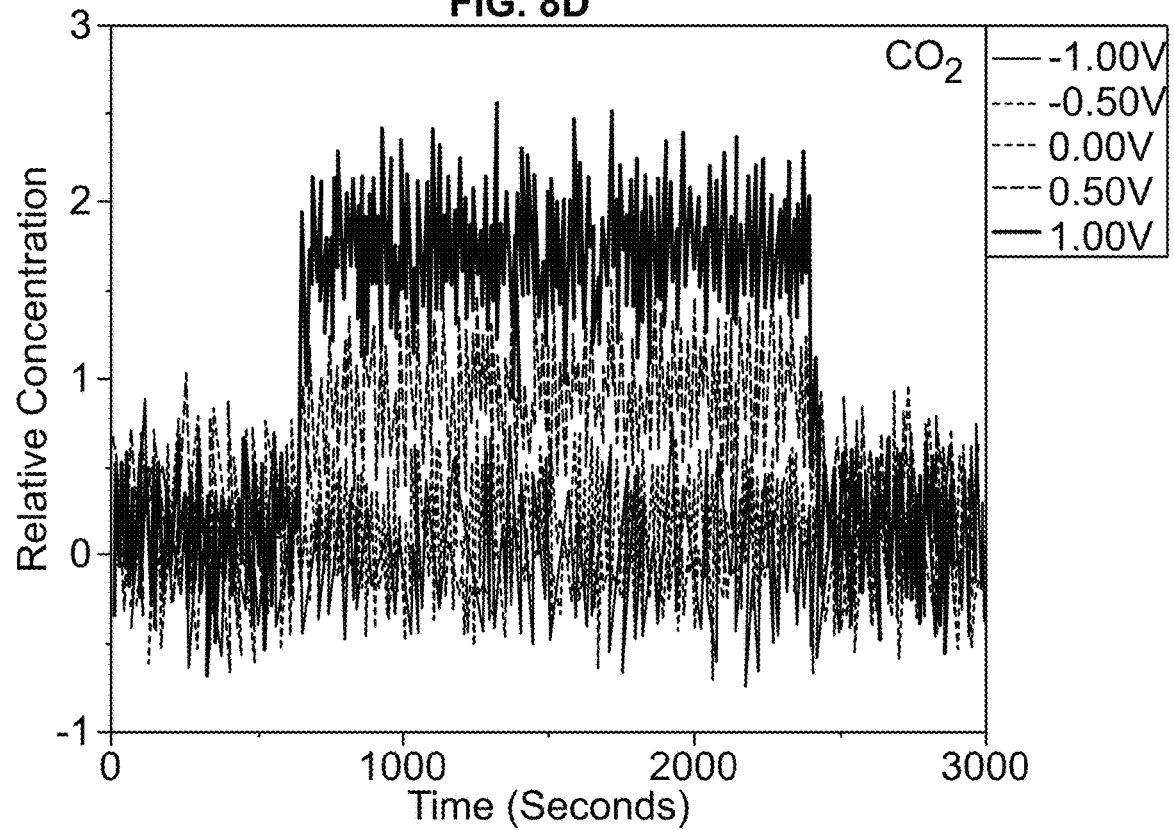

After establishing the chemical stability of BMNF perovskite and its catalytic activity towards methane activation through TGA, PXRD, and TPR measurements, electrochemical characterization of the BMNF perovskites was carried out. The conductivity plots obtained for the three BMNF pellets via electrochemical impedance measurements are given in FIG. 3a where a maximum conductivity of 17 mS $cm^{-1}$ was obtained for BMNF33 while that observed for BMNF17 is only 7 mS $cm^{-1}$. The parent $BaMg_{0.33}Nb_{0.67}O_{3-\delta}$ showed a negligible conductivity in the entire investigated temperature range despite aliovalent Mg doping on Nb sites. E-OCM measurements were carried out in a setup with LSGM as electrolyte (0.9 mm thickness and 20 mm diameter), 65:35 mixture of SFMO/GDC as the cathode and a 65:35 mixture of BMNF/GDC as the anode. The electrodes were brush painted on the LSGM pellet, before being sintered at 1175° C. to remove any impurities. LSGM was chosen for electrolyte as the SFMO tend to react with YSZ electrolyte. Cyclic voltammetry (CV) measurements carried out on this cell using BMNF25 as the anode at a scan rate of 1 mV/s in a wide potential window (−1.5V to 0.9V against the air reference electrode) is shown in FIG. 4 while the magnified plot between −1.5 V to 0.1 V is given in FIG. 3b. The CV plots indicate clear catalytic activity towards methane activation at very low overpotentials near −0.75 V. The full window scan measured between −1.5V and 1.0V shown in FIG. 4 indicate a linear rise in current from 0.0V to 1.0V that suggests a constant surge of oxide ions across the electrolyte that should aid the E-OCM process. The CVs further indicate the durability of BMNF25 under these harsh E-OCM conditions as no significant change in peak intensity or shape is observed over 10 hours of electrochemical cycling between −1.5 V to 1.0 V. The CV measurements taken after two days of continuous operation remained nearly identical (FIG. 5) further emphasizing the durability of BMNF25. For comparison, SFMO based electrodes lost all characteristic peaks within few CV cycles. CVs measured in 4% $H_2$ are given in FIG. 6 which indicate none of the characteristic peaks in the −1.3 to −0.5 V region obtained in methane environment. This further demonstrates the role of BMNF25 material in specifically activating methane in a well-defined electrochemical window. These peak position are similar to SFMO based electrodes which showed methane activation in the potential range of −0.75 V to −0.5 V. The outlet stream of the anode is analyzed continuously by mass spectroscopic measurements to understand the product distribution along with the role of applied bias on E-OCM. The CV results obtained for BMNF25 as a function of time along with the mass spectroscopy results are presented in FIG. 3c while that obtained for BMNF25 under 4% $H_2$ flow is presented in FIG. 7. The results clearly indicate the methane activation property of BMNF25 as ethylene and hydrogen is produced under pure $CH_4$. Interestingly, the methane activation products such as ethylene, $CO_2$, $H_2O$ and $H_2$ all reached their peak value at the maximum positive potential on the studied potential window i.e., 1.0 V. This is in contrast to previous results with SFMO-075Fe based electrodes where, ethylene production was peaked at −0.75 V in accordance with the methane activation peak in CV. This could possibly be due to the low conductivity of BMNF materials that has resulted in very low current densities at −0.75 V (>10 mA $cm^{-2}$) in comparison to currents at 1.0 V (~160 mA $cm^{-2}$).

The low currents could be due to a lower electronic conductivity of BMNF perovskites coupled with low surface area that is normally associated with high-temperature solid state synthesis. For example, the maximum conductivity obtained for BMNF25 through electrochemical impedance measurements is 13 $mScm^{-1}$ at 900° C. which is significantly lower than the conductivity of typical solid oxide electrode materials such as LSM which is about $5.5\times10^3$ S $m^{-1}$ at 800° C.

Chronoamperometric measurements on this cell once again showed quantifiable ethylene and hydrogen production only at high positive applied potentials (FIG. 8). A maximum ethylene production rate of 277.2 μmol $cm^{-2}$ $h^{-1}$ at a faradaic efficiency (FE) of 20% was observed at 1.0 V for this BMNF25 based cell while the FE for producing $CO_2$ was 39%. This is about four times higher than the faradaic efficiency obtained with SFMO electrode which produced mostly complete oxidation products such as $CO_2$ and $H_2O$. This result clearly indicates the propensity of this material to produce ethylene even at high applied biases that tend to favor $CO_2$ production. The FE towards $H_2O$ production could not be satisfactorily calculated due to water condensing in the lines and it's deteriorating effect on the mass spec instrument. While thermocatalytic activity inferred from TPR measurements indicated a methane activation temperature of about 600° C., E-OCM results are obtained at 925° C. due to the low electrical conductivity of BMNF. Nevertheless, both measurements indicated a better selectivity towards ethylene despite different operating temperatures.

Figure 9A:
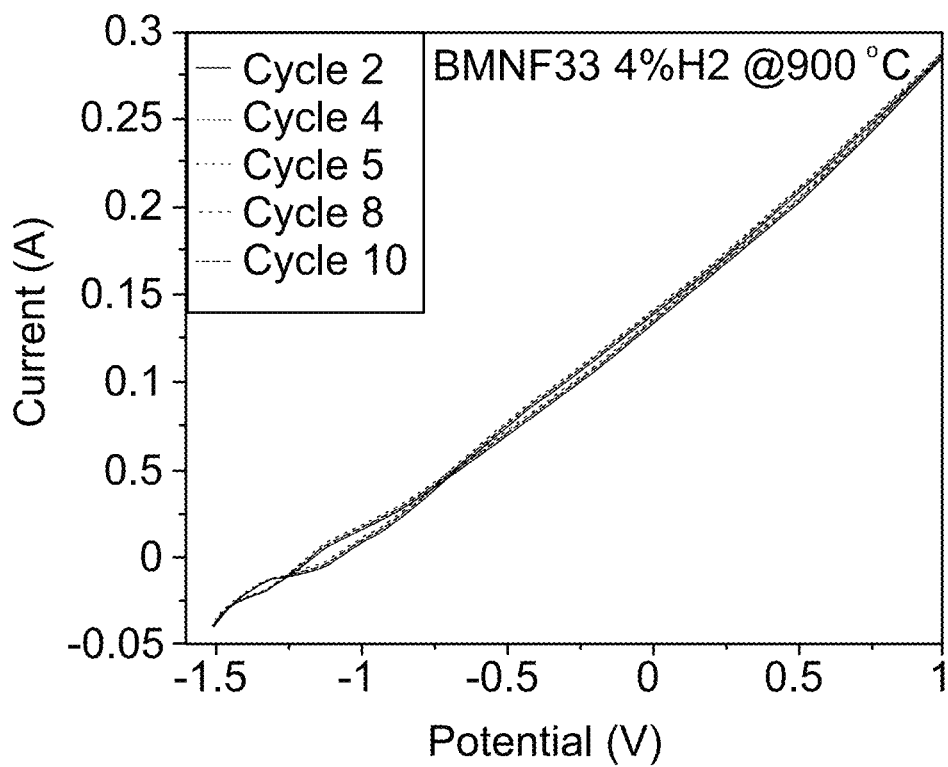
FIGS. 9A and 9B show CV curves obtained for BMNF33 electrode at 900° C. in a wide potential window of −1.5V to 1.0V at a scan rate of 1 mV/s under 100 SCCM of (a) UHP $CH_4$ feed, and (b) 4% $H_2$ balanced in $N_2$ to the anode. The cathode was maintained with 100 SCCM $O_2$ supply.
Figure 9B:
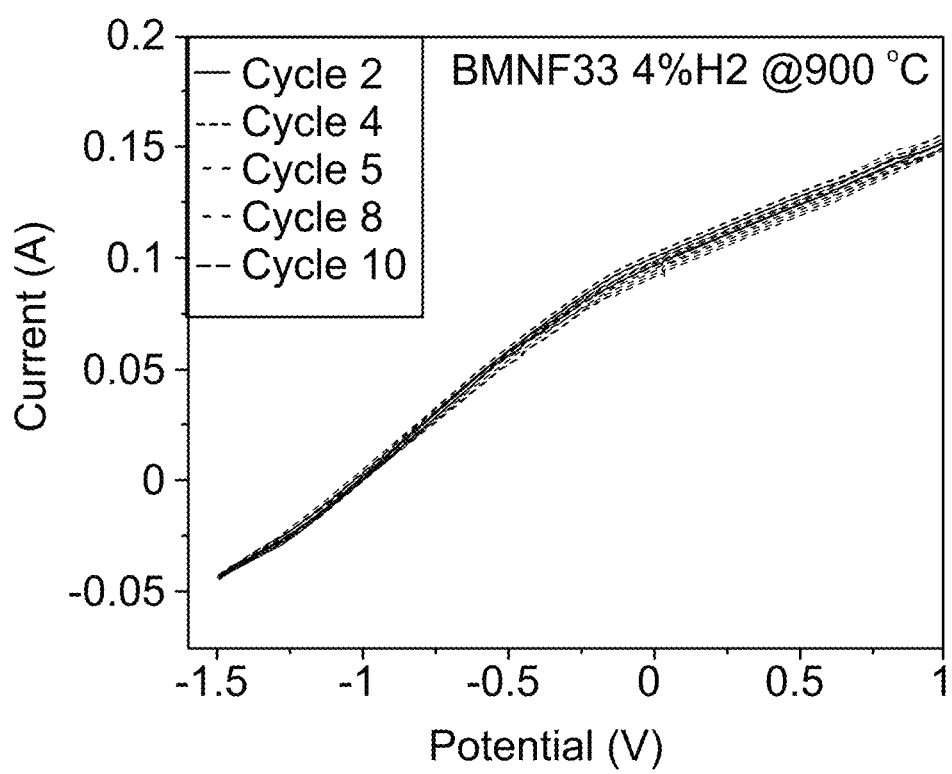

Interestingly, E-OCM measurements with the higher Fe doped perovskite BMNF33 as the electrode resulted in complete oxidation of methane and the product stream is dominated with $CO_2$ and $H_2O$ with significantly lower production of ethylene in comparison to both BMNF17 and BMNF25 based electrodes. The higher Fe doping in the BMNF33 could be a reason for this overoxidation of methane towards $CO_2$. However, the impurities $Mg_2Fe_2O_5$ observed in PXRD with BMNF33 could also have played a role in the overoxidation although it is not clear at this point. CV measurements with BMNF33 in $CH_4$ indicate less defined peaks while in 4% $H_2$ show no identifiable peaks (FIG. 9a and FIG. 9b) and mass spectra analysis of the outlet for BMNF33 electrode indicate complete oxidation products such as $CO_2$ in comparison to BMNF25. Chronoamperometric measurements for BMNF33 once again indicated the complete oxidation products such as $CO_2$ all indicating the adverse impact of higher Fe doping.

Figure 10A:
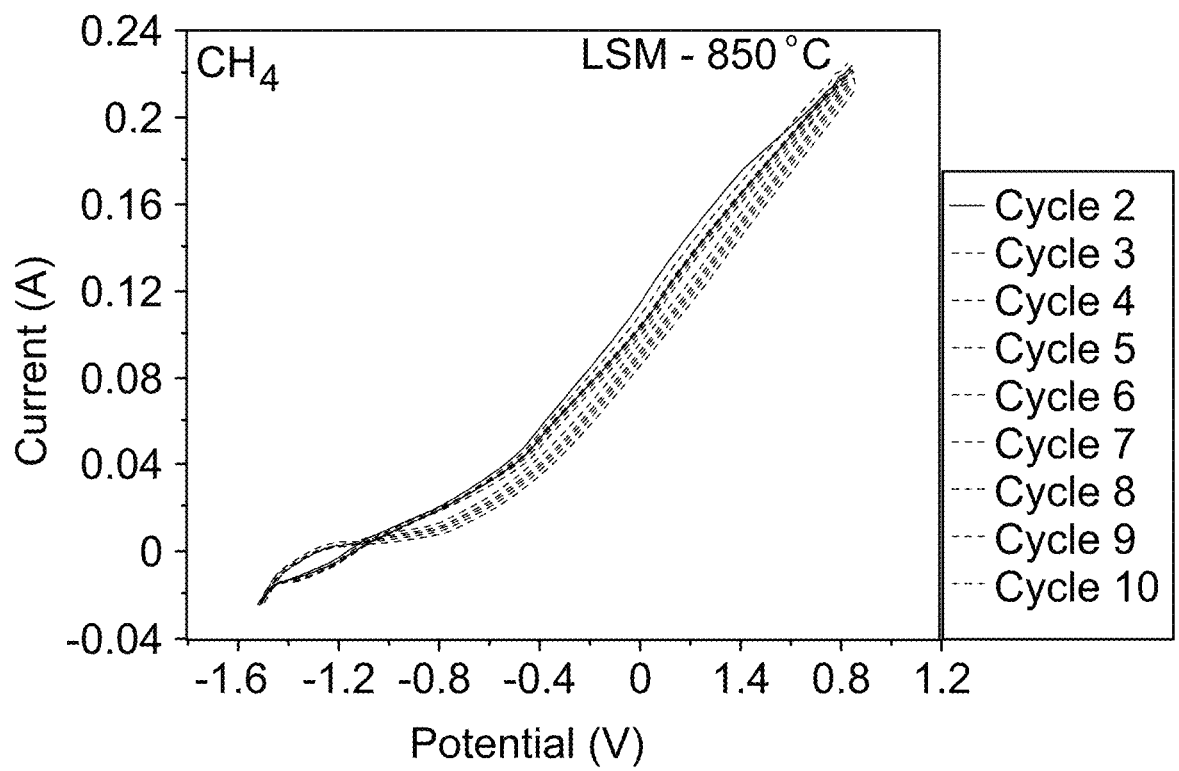
FIGS. 10A and 10B show CV curves obtained for commercial LSM electrode at 850° C. in a wide potential window of −1.5V to 1.0V at a scan rate of 1 mV/s under 100 SCCM of (a) UHP CH4 feed, and (b) 4% $H_2$ balanced in $N_2$ to the anode. The cathode was maintained with 100 SCCM $O_2$ supply.
Figure 10B:
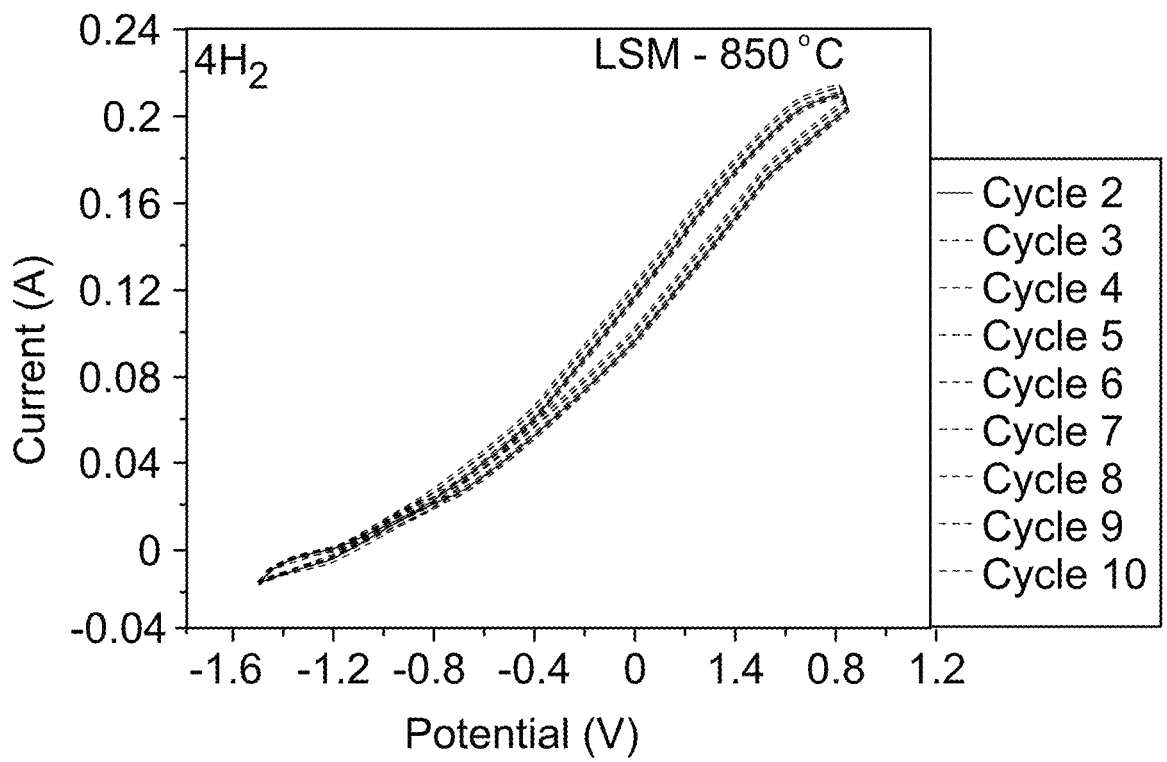

Nevertheless, BMNF perovskites showed remarkable chemical stability and maximum E-OCM activity was obtained with BMNF25. Further improvements in electrical conductivity as well as surface area are required for BMNF materials to fully utilize their methane activation properties toward ethylene production. For comparison, E-OCM measurements were carried out with commercial LSM catalyst as anode and CVs obtained under $CH_4$ and 4% $H_2$ are given in FIG. 10a and FIG. 10b. Both CVs are featureless in comparison to BMNF25 electrode under both $CH_4$ and 4% $H_2$ environments once again reaffirming the role of BMNF25 in activating methane.

Mechanistic Analysis

Figure 12A:
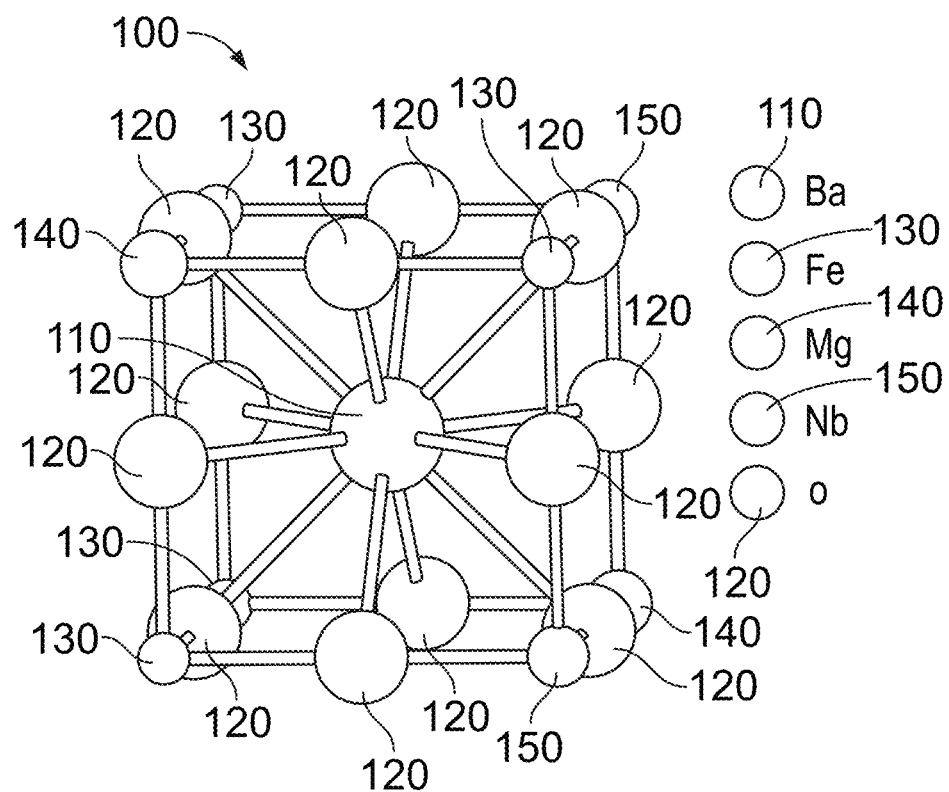
FIG. 12A is a crystalMaker view of the BMNF perovskite.

The cubic perovskite structure created in CrystalMaker® is given in FIG. 12a where both Mg and Fe are incorporated on the Nb site resulting in oxide ion vacancy creation. In a preferred embodiment as shown in FIG. 12a, a catalyst comprising a barium niobate-based cubic perovskite structure 100 where, Mg and Ca has been used to dope the niobium sites along with Fe. Cubic perovskite structure includes barium 110 at the center with oxygen 120 bonded thereto. Bonded to the oxygen 120 are Fe 130, Mg 140, and Nb 150.

The doping of $Mg^{2+}$ and $Fe^{3+}$ may occur at the Nb site as their Shannon ionic radii (0.72 Å and 0.645 Å respectively) matches better with Nb ($Nb^{4+}$-0.68 Å, $Nb^{5+}$-0.64 Å) than $Ba^{2+}$ (1.35 Å) which also support oxygen vacancy creation. XPS results obtained for BMN and BMNF33 are shown in FIG. 12c-12f. The incorporation of Mg on Nb sites in BMN has resulted in oxygen vacancy creation as about 50% of the oxygen atoms are partially coordinated that is attributable to neighboring oxygen vacancy. This partially coordinated oxygen concentration increased to 74.9% in BMNF33 indicating a further rise in oxygen vacancy upon Fe doping (Table 1):

TABLE 1

XPS quantification of the peaks corresponding to oxygen and Nb in the Mg only doped (BMN) and Mg and Fe codoped (BMNF) barium niobates.

| Material | O1 s fully coordinated (%) | O1 s Partially coordinated (%) | $Nb^{4+}$ (%) | $Nb^{5+}$ (%) |
|---|---|---|---|---|
| BMN | 49.7 | 50.3 | 94.8 | 5.2 |
| BMNF33 | 25.1 | 74.9 | 70.5 | 29.5 |

Interestingly, in BMN Nb is mainly in 4+ oxidation state with Nb in 5+ oxidation state contribution is only 5%. However, upon Fe doping $Nb^{5+}$ contribution has increased six-fold to about 30%. Ceramic materials with high acidic character are tend to be stable in carbonate forming environments. For example, the incorporation of acidic $Ti^{4+}$ ions in $SrCo_{0.8}Fe_{0.2}O_{3-\delta}$ is reported to show decreased carbonate formation in pure $CO_2$ environments at temperatures up to 950° C. Thus, the highly acidic $Nb^{4+}$ may be the reason for BMN's chemical stability.

Figure 12B:
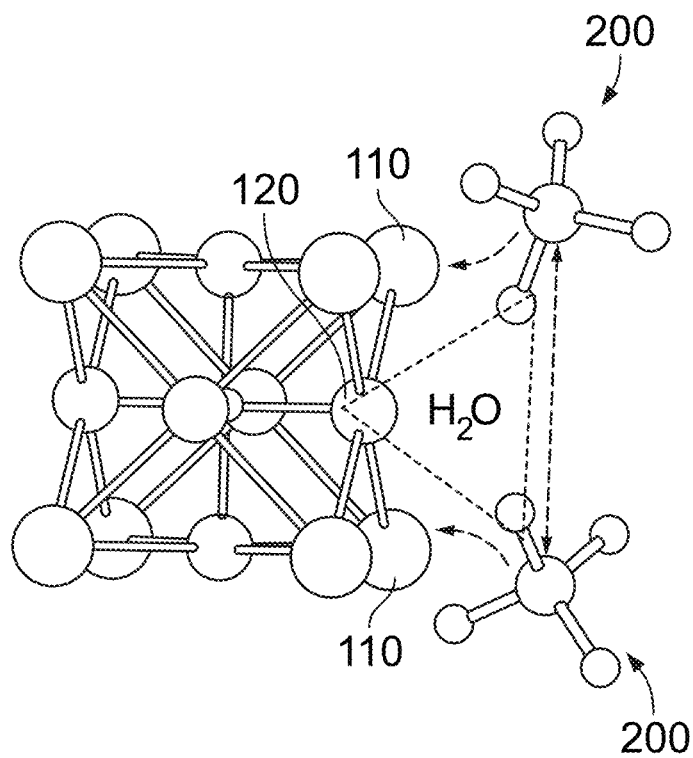
FIG. 12B is a schematic representation of methane adsorption on the Ba site in BMNF and water removal using adjacent O atom.
Figure 12C:
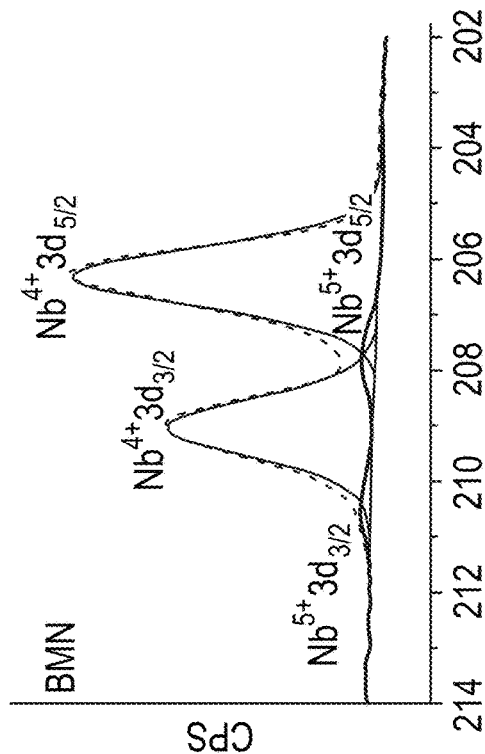
FIG. 12C is XPS data collected for O 1s for the BMN perovskite.
Figure 12D:
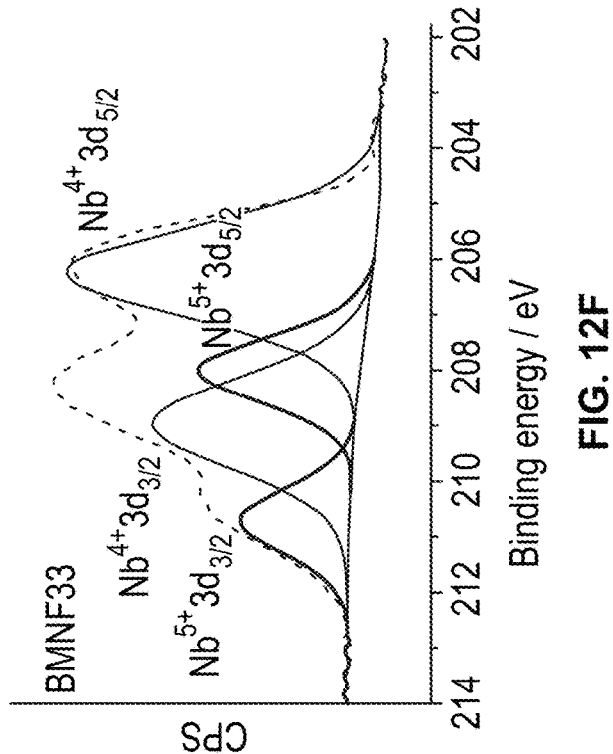
FIG. 12D is XPS data collected for Nb 3d for the BMN perovskite.
Figure 12E:
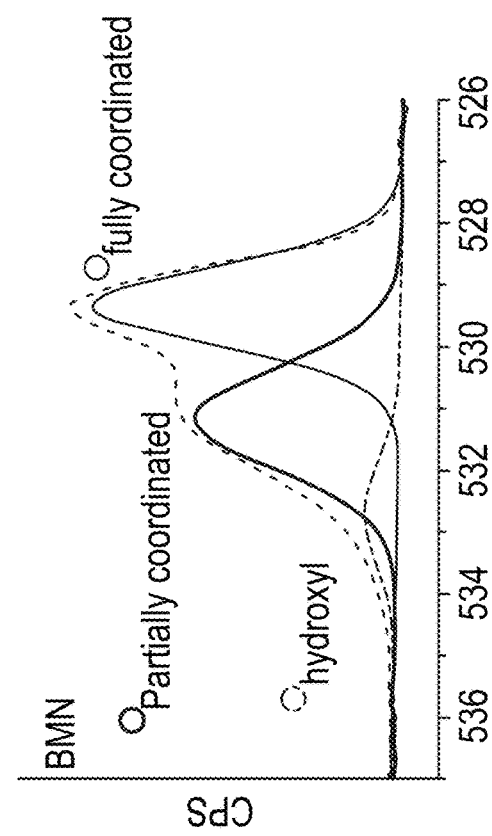
FIG. 12E is XPS data for O 1s for BMNF33 perovskite.
Figure 12F:
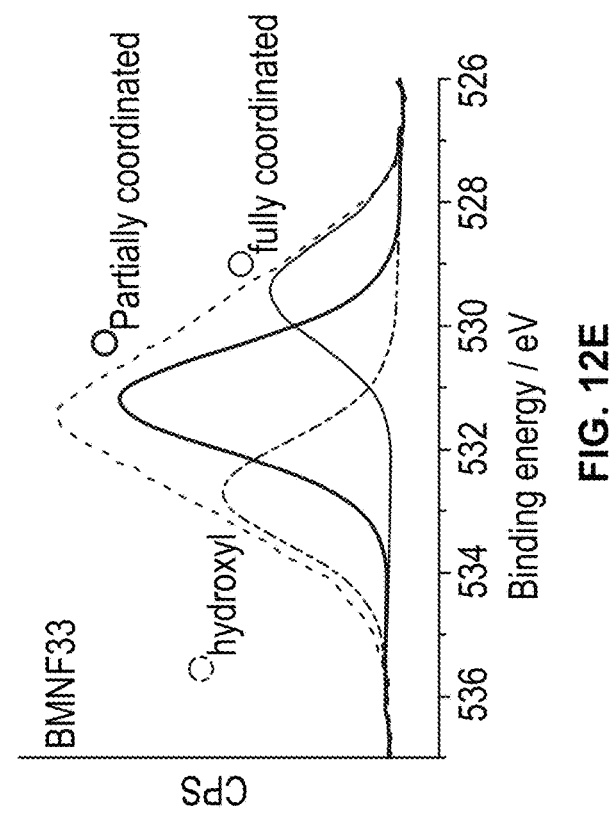
FIG. 12F is XPS Nb 3d data collected for BMNF33 perovskite.

Importantly, upon $Fe^{2+/3+}$ incorporation, part of $Nb^{4+}$ is converted to $Nb^{+5}$ that could provide further stability enhancement in carbonate forming environments. On the other hand, among alkaline earth metals, Ba is reported to adsorb methane, CO, and $CO_2$ in a wide variety of temperatures. BMNF has previously been reported for $CO_2$ sensing application in the temperature range of 500 to 700° C. As shown in FIG. 12b, barium sites 110 in BMNF act as adsorption sites for methane 200 while adjacent lattice oxygen 120 help remove two hydrogen atoms as water as shown in the scheme. This type of surface oxide ions ($O^-$) reacting with methane is well-known for metal oxide catalysts. However, a continuous removal of surface oxygen and hydrogen from methane will lead to crystal structure collapse, loss of activity, and coke formation. However, no change in BMNF crystal structure was observed and no coke formation was observed either ruling out the continuous removal of oxygen atom from the site. This could occur due to the higher $Nb^{5+}$ concentration that would increase the attraction towards the negative oxide ions and resist their continuous removal.

Figure 11A:
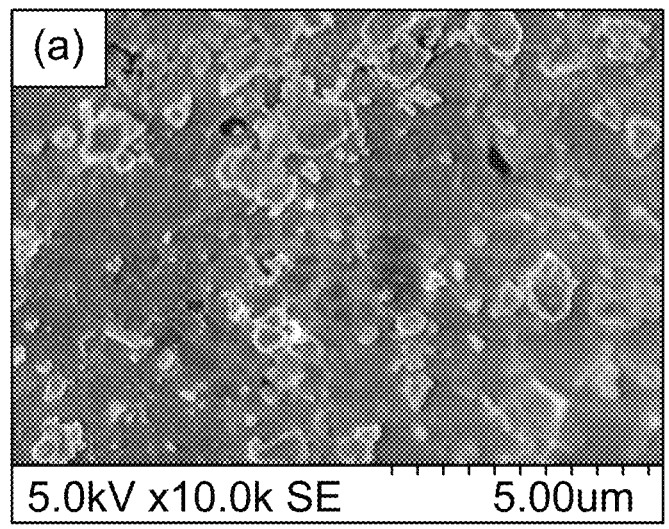
FIGS. 11A and 11B are SEM images obtained for (a) as-prepared BMNF33 and (b) after exposure to pure CH4 at 900° C. for one hour.
Figure 11B:
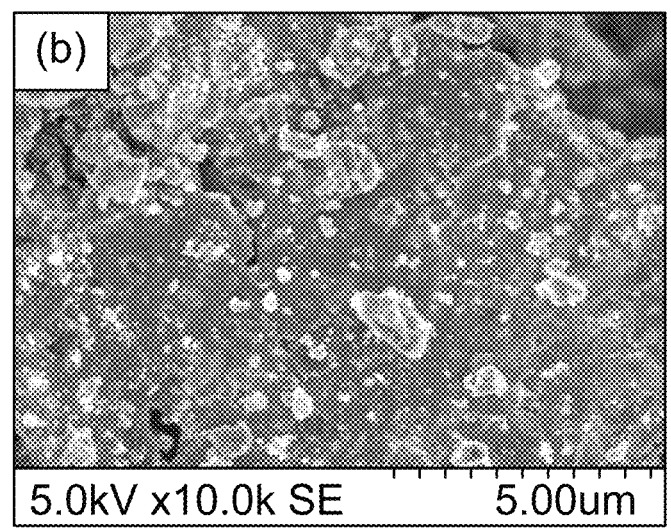

Similarly, Ba based metal oxides are known to form barium carbonate under carbon rich conditions due to the higher stability of $BaCO_3$ under these conditions. Nevertheless, the BMNF perovskite has remained stable under these carbon rich environment and no carbonate or coke formation was observed either. The oxygen mobility in this cubic perovskite is very limited which may have helped to preserve the crystal structure and the surface oxygen has to be replenished with incoming oxide ions (E-OCM) or oxygen molecule (OCM) for sustained catalytic activity. This is supported by the fact that despite significant oxygen vacancies as evidenced from XPS measurements, BMN show poor conductivity (>1 μS/cm). The low oxide ion mobility and the higher acidity associated with $Nb^{4+/5+}$ ions may have helped reduce both coke formation and carbonate formation. The presence of Nb tends to increase stability under SOFC operating conditions due to its redox stability. SEM images obtained for as-prepared and $CH_4$ exposed samples do not show any morphological change or carbon deposition in EDS measurements (FIG. 11). Another mode of methane activation utilizing oxide ion conducting membranes is the Non-Faradaic Electrochemical Modification of Catalytic Activity (NEMCA) which is normally associated with Faradaic efficiencies much higher than 100%. However about 20% Faradaic efficiency for ethylene production was observed indicating the absence of NEMCA mechanism in the E-OCM measurements.

The high chemical stability along with methane activation properties observed for BMNF perovskites open new opportunities for fine tuning its catalytic activity through various dopants and can also be used as a support for conventional methane activation catalysts where catalyst-support synergy could help achieve better conversion and selectivity towards desired products.

Mg and Fe co-doped barium niobates were synthesized for application in E-OCM. Chemical stability studies by TGA, PXRD, and TPR all revealed that all the three prepared compositions possess good chemical stability under conditions relevant for E-OCM. The chemical stability could be due to the increased acidity of $Nb^{4+/5+}$ ions in the crystal lattice. TPR measurements further revealed that the onset of ethylene production at about 600° C. that is significantly lower than well known OCM catalysts. E-OCM measurements were operated at much higher temperatures in order to get good oxide ion conductivity in BMNF revealed about four times higher faradaic efficiency towards ethylene production than SFMO electrodes at 1.0V indicating this materials unique ability to selectively produce ethylene even under extremely oxidizing conditions. XPS measurements indicate a possible valency reorganization for Nb in Fe doped BMNF compositions that improve the chemical stability. The results demonstrating the methane activation properties of BMNF along with its unique chemical stability under carburizing environments open up new avenues for finding a better catalyst for methane activation under different methodologies.

Materials:

$BaMg_{0.33}Nb_{0.67-x}Fe_xO_{3-\delta}$ (BMNF) was formed from the following precursors: $BaCO_3$, $C_4Mg_4O_{12} \cdot H_2MgO_2 \cdot 5H_2O$ (Magnesium carbonate hydroxide pentahydrate), $Nb_2O_5$, and $Fe_2O_3$. The electrolyte material $La_{0.9}Sr_{0.1}Ga_{0.8}Mg_{0.2}O_{3-\delta}$ (LSGM), and $Ce_{0.8}Gd_{0.2}O_2$ (GDC) were purchased from Millipore Sigma®. Gold Wire used as the leads in the electrochemical cell was purchased from Rio Grande Jewelry Supply®. Silver mesh current collectors, high temperature sealing paste (CAP552), thinner for high temperature sealing paste (CAP-552-T), alumina slurry (ALSL), and alumina felt seals were purchased from Fuel Cell Materials®. Alumina tubes were purchased from AdValue Technology®.

Material synthesis: The perovskite anode material $BaMg_{0.33}Nb_{0.67-x}Fe_xO_{3-\delta}$, was produced using solid-state synthesis methods. Initially, the metal oxide and metal carbonate precursors were weighed in stoichiometric ratios to produce 7 grams of $BaMg_{0.33}Nb_{0.67-x}Fe_xO_{3-\delta}$ with x values of 0.33, 0.25, 0.17, and 0.00 corresponding to BMNF33, BMNF25, BMNF17 and BMN respectively. The metal oxide precursors were added to a zirconia ball-milling jar and isopropyl alcohol (IPA) (30 mL) was added (as liquid for ball milling). Each jar contained 16 individual 10 mm diameter Zirconia milling balls and powder was milled for 6 hours. After milling, ball-milling jars were dried at 120° C. in an oven. The dried powders were calcined at 1000° C. using a 12 hour hold and 5° C. $minute^{-1}$ heating and cooling rate in a three-phase furnace. The calcined powders were further ball milled for 6 hours in IPA followed by drying at 120° C. Thus, obtained powders were pressed into 2 individual pellets using a 12 mm die. Both uniaxial pressing, followed by isostatic pressing were used. The initial uniaxial pressing is done at 1000 psi for 3 minutes followed by isostatic pressing done at 240 MPa for 3 minutes. Each pressed pellet weighed about 2.0 grams. The pellets were soaked in excess parent powder in an alumina crucible for calcining. The pellets are calcined at 1400° C. for 24 hours with a 5° C. $minute^{-1}$ heating and cooling rate in a Carbolite tube furnace. After this process, the pellets were used for further measurements. BMNF powder is typically black in color, with lighter shades corresponding to a lower iron concentration. The Fe free BMN was yellowish in color. The cathode $Sr_2Fe_{1.5}Mo_{0.5}O_{6-\delta}$ (SFMO) powders were prepared by a microwave assisted combustion methods. SFMO was chosen due to its very high electrical conductivity and compatibility with LSGM. The LSGM pellets for electrolyte application are prepared from commercially obtained LSGM powder. About 1.6 g of LSGM powder was pressed uniaxially using a 25 mm die. The pressed powder was then pressed in the isostatic press at 240 MPa for three minutes followed by sintering at 1175° C. for 12 hours using a 3° C. $minute^{-1}$ heating and cooling rate.

Physical Characterization:

BMNF powders were characterized by powder X-ray diffraction (PXRD), thermogravimetric analysis (TGA), scanning electron microscopy (SEM), and X-ray photoelectron spectroscopic (XPS) measurements. TGA was carried out in air and in pure methane environments. TGA measurements were carried out using TA Q600 SDT instrument in air and in pure methane environments with flow rate of 50 ml-pm in the temperature window of 25° C. to 900° C. at a heating and cooling rate of 5° C. $minute^{-1}$ and held at 900° C. for one hour. XPS measurements were performed on a Kratos Ultra DLD spectrometer using a monochromatic Al $K\alpha$ source operating at 150 W (1486.6 eV). The operating pressure was $5 \times 10^{-9}$ Torr. Survey spectra were acquired at a pass energy of 160 eV and high-resolution spectra were acquired at a pass energy of 20 eV. XPS data was processed using Casa XPS software. X-ray diffraction measurements were done in a PANalytical Xpert Pro instrument using Cu $K\alpha$ radiation and operating at 40 kV and 40 mA on a zero-background holder. SEM-EDX measurements carried out on Hitachi S-5200 scanning electron microscope.

Electrochemical Measurements:

BMNF (200 mg) is mixed with $Ce_{0.8}Gd_{0.2}O_2$ (GDC) (100 mg), terpineol (630 mg), and cellulose (70 mg) to produced 1 g of BMNF ink. This mixture is probe sonicated using a Tekmar probe sonicator for 6 minutes in 30 second intervals (on/off). The SFMO cathode was made using SFMO (200 mg) and GDC (100 mg) with terpineol (630 mg) as a dispersant and cellulose (70 mg) added for induced porosity. The resultant mixture is ultrasonically mixed before electrode painting. The BMNF anode is brush-coated onto the LSGM electrolyte in a 1×1 $cm^2$ electrode area. 3 layers of material are coated onto the electrolyte, with a heat gun used to dry each subsequent layer. The SFMO cathode is brush-coated with the same specifications. This cell is placed into a 3-phase furnace and heat-treated at 1175° C. for 12 hours in air at a 3° C. $minute^{-1}$ heating rate. After heat treatment, silver mesh current collectors were applied to both the anode and cathode of this cell. Each silver mesh current collector is interwoven with the gold leads and is attached to the respective electrode using silver paste. After the silver paste dries (for at least 20 minutes), the cell is placed on the alumina tube setup using the high-temperature sealing paste mixed with thinner, along with an alumina felt seal to make a leak-free attachment of the cell to the alumina tubing. The cell is left in the open-air environment for four or more hours (to allow for the paste to dry) and placed in the cell-testing furnace. Here, the cell undergoes in-situ heat treatment at 95° C. and 260° C. for two hours each, followed by sintering at 550° C. for an hour. The cell is then heated to 800° C. after which a 100 SCCM of 4% $H_2$ balanced in $N_2$ is introduced anode-side and 100 SCCM of UHP $O_2$ is introduced to the cathode side. After contact with the catalyst of the claimed invention for one hour under 4% $H_2$, 100 SCCM UHP $CH_4$ is introduced to the anode side for electrochemical oxidative coupling of methane experiments. The outlet of the EC-OCM set up is continuously fed into a Cirrus mass spectrometer for regular monitoring and periodically analyzed by an SRI 8610C Gas chromatography instrument. Electrochemical experiments were carried out using a Gamry reference 600 instrument.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above-described embodiments, methods, and examples, but by all embodiments and methods within the scope and spirit of the disclosure.

What is claimed is:

1. A catalyst comprising: a barium niobate-based cubic perovskite structure where, Mg and Ca has been used to dope the niobium sites along with Fe, Ni, Co, Y, and Pr.

2. The catalyst of claim 1 wherein said barium niobate-based cubic perovskite structure has the chemical formula of $BaCa_{0.33}Nb_{0.67-x}M_xO_{3-\delta}$ and $BaMg_{0.33}Nb_{0.67-x}M_xO_{3-\delta}$ where M is one or more of Fe, Co, Ni, Y, or Pr and the M content is varied from x=0 to x=33.

3. The catalyst of claim 1 wherein said barium niobate-based cubic perovskite structure has the chemical formula of $BaCa_{0.33}Nb_{0.67-x}Fe_xO_{3-\delta}$ and $BaMg_{0.33}Nb_{0.67-x}Fe_xO_{3-\delta}$.

4. The catalyst of claim 3 wherein the Fe content is varied from x=0 to x=33.

5. The catalyst of claim 4 wherein said Mg and said Fe are incorporated on said Nb site resulting in oxide ion vacancy creation.

6. The catalyst of claim 4 wherein said barium sites act as adsorption sites for methane while adjacent lattice oxygen remove two hydrogen atoms as water.

7. The catalyst of claim 3 wherein the Fe content is varied from x=0 to x=60.

8. A catalyst for oxidizing methane comprising: a barium niobate-based cubic perovskite structure where, Mg and Ca has been used to dope the niobium sites along with Fe.

9. The catalyst of claim 8 wherein said barium niobate-based cubic perovskite structure has the chemical formula of $BaCa_{0.33}Nb_{0.67-x}Fe_xO_{3-\delta}$ and $BaMg_{0.33}Nb_{0.67-x}Fe_xO_{3-\delta}$.

10. The catalyst of claim 9 wherein the Fe content is varied from x=0 to x=33.

11. The claim of catalyst 9 wherein the Mg and Ca content is varied from 0.20 to 0.40.

12. The catalyst of claim 9 wherein said Ca and said Fe are incorporated on said Nb site resulting in oxide ion vacancy creation.

13. The catalyst of claim 9 wherein said barium sites act as adsorption sites for methane while adjacent lattice oxygen remove two hydrogen atoms as water.

14. The catalyst of claim 9 wherein the Fe content is varied from x=0 to x=60.

15. The catalyst of claim 8 wherein said barium niobate-based cubic perovskite structure has the chemical formula of $BaCa_{0.33}Nb_{0.67-x}M_xO_{3-\delta}$ and $BaMg_{0.33}Nb_{0.67-x}M_xO_{3-\delta}$ where M is one or more of Fe, Co, Ni, Y, or Pr and the M content is varied from x=0 to x=60.

16. A method for the oxidation of methane comprising: providing a feed comprising said light hydrocarbon mixtures; and
contacting said feed with a catalyst comprising a barium niobate-based cubic perovskite structure where, Mg and Ca has been used to dope the niobium sites along with Fe.

17. The method of claim 16 wherein said barium niobate-based cubic perovskite structure has the chemical formula of $BaCa_{0.33}Nb_{0.67-x}Fe_xO_{3-\delta}$ and $BaMg_{0.33}Nb_{0.67-x}Fe_xO_{3-\delta}$.

18. The method of claim 16 wherein the Fe content is varied from x=0 to x=60.

19. The method of claim 17 wherein said Mg and said Fe are incorporated on said Nb site resulting in oxide ion vacancy creation.

20. The method of claim 17 wherein said barium sites act as adsorption sites for methane while adjacent lattice oxygen remove two hydrogen atoms as water.

21. The method according to claim 17, further comprising maintaining said catalyst at a temperature between about 200° C. and about 1000° C.

* * * * *